US009617544B2

(12) United States Patent
Cheng et al.

(10) Patent No.: US 9,617,544 B2
(45) Date of Patent: Apr. 11, 2017

(54) NANOPARTICLE MEDIATED DELIVERY OF SIRNA

(71) Applicant: The Board of Trustees of the University of Illinois, Urbana, IL (US)

(72) Inventors: Jianjun Cheng, Champaign, IL (US); Lichen Yin, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/783,765

(22) PCT Filed: Apr. 11, 2014

(86) PCT No.: PCT/US2014/033888
§ 371 (c)(1),
(2) Date: Oct. 9, 2015

(87) PCT Pub. No.: WO2014/169264
PCT Pub. Date: Oct. 16, 2014

(65) Prior Publication Data
US 2016/0076038 A1 Mar. 17, 2016

Related U.S. Application Data

(60) Provisional application No. 61/810,983, filed on Apr. 11, 2013.

(51) Int. Cl.
*C12N 15/11* (2006.01)
*C07H 21/04* (2006.01)
*C12N 15/113* (2010.01)
*A61K 9/51* (2006.01)

(52) U.S. Cl.
CPC ........ *C12N 15/1136* (2013.01); *A61K 9/5115* (2013.01); *C12N 15/111* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| 8,461,316 B1 | 6/2013 | Sung et al. |
| 2011/0082092 A1 | 4/2011 | Chatterton |
| 2011/0142767 A1 | 6/2011 | Yanni et al. |
| 2013/0178421 A1 | 7/2013 | Yu et al. |

FOREIGN PATENT DOCUMENTS

WO 2012019121 A2 2/2012

OTHER PUBLICATIONS

Amarzguioui, Mohammed et al., "Rational design and in vitro and in vivo delivery of Dicer substrate siRNA," Nature Protocols, 2006, 508-517, 1.
Aouadi, Myriam et al., "Orally delivered siRNA targeting macrophage Map4k4 suppresses systemic inflammation," Nature, 2009, 1180-1185, 458.
Dong, Lei et al., "Targeting delivery oligonucleotide into macrophages by cationic polysaccharide from Bletilla striata successfully inhibited the expression of TNF-α," Journal of Controlled Release, 2009, 214-220, 134.
Gabrielson, Nathan P. et al., "A cell-penetrating Helical Polymer for siRNA Delivery to Mammalian Cells," Molecular Therapy, 2012, 1599-1609, 20.
Gabrielson, Nathan P. et al., "Multiplexed supramolecular self-assembly for non-viral gene delivery," Biomaterials, 2010, 9117-9127, 31.
Gabrielson, Nathan P. et al., "Reactive and Bioactive Cationic a-Helical Polypeptide Template for Nonviral Gene Delivery," Angewandte Chemie (International ed. in English), 2012, 1143-1147, 51.
Howard, Kenneth A. et al., "Chitosan/siRNA Nanoparticle-mediated TNF-α Knockdown in Peritoneal Macrophages for Anti-inflammatory Treatment in a Murine Arthritis Model," Molecular Therapy, 2009, 162-168, 17.
International Search Report dated Sep. 12, 2014; Application No. PCT/US14/33888, filed Apr. 11, 2014.
Kuhla, Angela et al., "Role of the perforin/granzyme cell death pathway 1n D-Gal/LPS-induced inflammatory liver injury," American Journal of Physiology—Gastrointestinal Liver Physiology, 2009, G1069-G1076, 296.
Lu, Hua et al., "Ionic polypeptides with unusual helical stability," Nature Communications, 2011, 1-9, 2.
Lundberg, Patric et al., "Protection against TNFα-dependent liver toxicity by intraperitoneal liposome delivered DsiRNA targeting TNFα in vivo," Journal of Controlled Release, 2012, 194-199, 160.
Sonia, T.A. et al., "Chitosan and Its Derivatives for Drug Delivery Perspective," Advances in Polymer Sciences, 2011, 23-54, 243.
Un, Keita et al., "Efficient Suppression of Murine Intracellular Adhesion Molecule-1 Using Ultrasound-Responsive and Mannose-Modified Lipoplexes Inhibits Acute Hepatic Inflammation," Hepatology, 2012, 259-269, 56.
Wang, Hao et al., "A Supramolecular Approach for Preparation of Size-Controlled Nanoparticles," Angewandte Chemie (International ed. in English), 2009, 4344-4348, 48.
Written Opinion dated Sep. 12, 2014; Application No. PCT/US14/33888, filed Apr. 11, 2014.
Yin, Lichen et al., "Supramolecular Self-Assembled Nanoparticles Mediate Oral Delivery of Therapeutic TNF-a siRNA against Systemic Inflammation," Angewandte Chemie (International ed. in English), 2013, 5757-5761, 52.
Yin, Lunxiang et al., "Sonochemical Synthesis of Cerium Oxide Nanoparticles—Effect of Additives and Quantum Size Effect," Journal of Colloid and Interlace Science, 2002, 78-84, 246.

*Primary Examiner* — Dana Shin
(74) *Attorney, Agent, or Firm* — Haukaas Fortius PLLC; Michael H. Haukaas

(57) ABSTRACT

The invention provides multifunctional supramolecular self-assembled nanoparticles (SSNPs) comprising a set of rationally designed components that collectively facilitate efficient intestinal absorption of siRNA. The nanoparticles can induce potent TNF-α silencing in macrophages. Single gavage of SSNPs in mice depleted systemic TNF-α production at an siRNA dose as low as 50 μg/kg, and protected the mice from lipopolysaccharide-induced hepatic injury.

17 Claims, 11 Drawing Sheets

```
                        SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gucucagccu cuucucauuc cugct                                            25

<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: misc_feature
<222> LOCATION: (9)..(9)
<223> OTHER INFORMATION: 2'-O-methyl modified
<220> FEATURE:
<221> NAME/KEY: misc_feature
<222> LOCATION: (11)..(11)
<223> OTHER INFORMATION: 2'-O-methyl modified
<220> FEATURE:
<221> NAME/KEY: misc_feature
<222> LOCATION: (13)..(13)
<223> OTHER INFORMATION: 2'-O-methyl modified
<220> FEATURE:
<221> NAME/KEY: misc_feature
<222> LOCATION: (15)..(15)
<223> OTHER INFORMATION: 2'-O-methyl modified
<220> FEATURE:
<221> NAME/KEY: misc_feature
<222> LOCATION: (17)..(17)
<223> OTHER INFORMATION: 2'-O-methyl modified
<220> FEATURE:
<221> NAME/KEY: misc_feature
<222> LOCATION: (19)..(19)
<223> OTHER INFORMATION: 2'-O-methyl modified
<220> FEATURE:
```

```
<221> NAME/KEY: misc_feature
<222> LOCATION: (21)..(21)
<223> OTHER INFORMATION: 2'-O-methyl modified
<220> FEATURE:
<221> NAME/KEY: misc_feature
<222> LOCATION: (23)..(23)
<223> OTHER INFORMATION: 2'-O-methyl modified
<220> FEATURE:
<221> NAME/KEY: misc_feature
<222> LOCATION: (25)..(27)
<223> OTHER INFORMATION: 2'-O-methyl modified

<400> SEQUENCE: 2
agcaggaaug agaagaggcu gagacau                                        27

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uucuccgaac gugucacgut t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
acgugacacg uucggagaat t                                              21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccaccacgct ctttctgtct actg                                           24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggctacagg cttgtcactc g                                              21
```

NANOPARTICLE MEDIATED DELIVERY OF SIRNA

RELATED APPLICATIONS

This application is a National Stage filing under 35 U.S.C. §371 of International Application No. PCT/2014/033888, filed Apr. 11, 2014, which claims priority under 35U.S.C. §119(e) to U.S. Provisional Patent Application No. 61/810,983, filed Apr. 11, 2013, which applications are is incorporated herein by reference.

GOVERNMENT SUPPORT

This invention was made with government support under contract numbers OD007246 and EB013379 awarded by the National Institutes of Health and contract number CHE1153122 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jun. 27, 2014, is named 500-034US1—SequenceListing.txt and is 2,648 bytes in size.

BACKGROUND OF THE INVENTION

Intervention of the inflammation cascade with tumor necrosis factor-α (TNF-α) monoclonal antibodies or receptors represents a major approach in clinical immunotherapy against inflammatory diseases. However, this approach often suffers from high cost, autoimmunity to antibodies, and various side effects. siRNA-mediated RNA interference (RNAi) has recently emerged as a potent modality in regulating gene expression by suppressing mRNA translation. Its high efficiency and specificity has made it a promising treatment paradigm for TNF-α-mediated inflammatory disorders. The therapeutic potential of siRNA was recently exemplified by a report of attenuating systemic inflammation by targeting orally delivered Map4k4 siRNA to gut-associated macrophages (GAMs). Owing to the infiltration of GAMs to systemic reticulo-endothelial tissues, Map4k4 siRNA-mediated TNF-α knockdown in GAMs extended to other tissues and thus induced systemic anti-inflammatory effects (Aouadi et al., Nature 2009, 458, 1180).

Despite its biological potency, the clinical potential of orally delivered siRNA has been hampered by the lack of efficient delivery technologies. siRNA is anionic, hydrophilic, and easily degraded by nucleases in the body. As such, it cannot survive the harsh condition of the gastrointestinal (GI) tract or effectively penetrate the intestinal epithelia or membranes of target cells. Hence, an effective carrier is needed not only to protect siRNA from degradation in the GI tract but also to improve the intestinal absorption as well as transfection in macrophages, thereby maximizing the in vivo RNAi efficiency and anti-inflammatory effect of orally delivered siRNA.

SUMMARY

To address the dearth of oral siRNA delivery technology, supramolecular self-assembled nanoparticles (SSNPs) have been developed. The SSNPs are able to overcome the absorption and transfection barriers posed by intestinal macrophages and exhibit remarkable in vivo oral RNAi efficiency. SSNPs were constructed via the electrostatic and hydrophobic self-assembly of several rationally designed or selected building blocks, as described herein.

Accordingly, the invention provides a nanoparticle comprising a cationic intestinal absorption enhancer; a cationic α-helical polypeptide; a mannose receptor targeting agent; a mucoadhesion agent; and an ionic crosslinking agent for stabilizing the nanoparticle. The nanoparticle can also include genetic material such as siRNA, and/or a therapeutic agent such as a drug. The nanoparticle can have a diameter of about 20 nm to about 600 nm or larger, but preferably about 80 nm to about 200 nm.

In some embodiments, the intestinal absorption enhancer is a chitosan polymer comprising quaternary ammonium moieties and $(C_{10}-C_{24})$alkyl amide moieties. The alkyl can be optionally branched, can be cyclic or include a cyclic alkyl group, can be optionally unsaturated at one or more sites, or a combination thereof. In one specific embodiment, the intestinal absorption enhancer is oleyl trimethyl chitosan (OTMC).

In some embodiments, the cationic α-helical polypeptide comprises polyglutamate or polylysine wherein the carboxyl moiety of the monomer side-chains are conjugated with one or more cationic groups (or groups that can be cationic at physiological conditions, e.g., of the stomach). In one specific embodiment, the cationic α-helical polypeptide is poly(γ-(4-(((2-(piperidin-1-yl)ethyl)amino)methyl)benzyl-$_L$-glutamate) (PVBLG-8).

In some embodiments, the mannose receptor targeting agent comprises a mannose moiety and a $(C_{10}-C_{24})$alkyl moiety linked by poly(ethylene glycol) (PEG). The alkyl can be optionally branched, can be cyclic or include a cyclic alkyl group, can be optionally unsaturated at one or more sites, or a combination thereof. The PEG linker can be any suitable and effective length, such as a chain having a molecular weight of about 0.5 kDa to about 50 kDa, about 1 kDa to about 10 kDa, about 2 kDa to about 5 kDa, or about 3-4 kDa. In one specific embodiment, the mannose receptor targeting agent is oleyl-PEG-mannose (OPM).

In some embodiments, the mucoadhesion agent comprises a thiol moiety and a $(C_{10}-C_{24})$alkyl moiety linked by poly(ethylene glycol) (PEG). The alkyl can be optionally branched, can be cyclic or include a cyclic alkyl group, can be optionally unsaturated at one or more sites, or a combination thereof. The PEG linker can be any suitable and effective length, such as a chain having a molecular weight of about 0.5 kDa to about 50 kDa, about 1 kDa to about 10 kDa, about 2 kDa to about 5 kDa, or about 3-4 kDa. In one specific embodiment, the mucoadhesion agent is oleyl-PEG-cysteamine (OPC).

In some embodiments, the ionic crosslinking agent is an anionic crosslinking agent. The anionic crosslinking agent can include phosphate moieties that electrostatically bind to the cationic intestinal absorption enhancer, the cationic α-helical polypeptide, or both. In one specific embodiment, the ionic crosslinking agent is sodium tripolyphosphate (TPP).

In some embodiments, the intestinal absorption enhancer/α-helical polypeptide/genetic material components of the nanoparticle are present in a ratio of about 100:20:1 (w/w). The values of the ratio can be independently varies +/−10% or +/−25%. In some embodiments, the intestinal absorption enhancer/crosslinking agent components of the nanoparticle are present in a ratio of about 8:1 (w/w). Any suitable and effective ratio of 20:1 to 1:10 can be employed, but preferably the ratio is about 6:1 to about 8:1. In some embodiments, the intestinal absorption enhancer/mannose receptor targeting agent/mucoadhesion agent components of the nanoparticle are present in a ratio of about 1:1:1 (w/w). In various embodiments, each integer can independently be 1, 2, 3, 4, 5, 6, 7, 8, 9, or 10.

In some embodiments, the nanoparticle has a diameter of about 20 nm to about 900 nm, about 80 nm to about 600 nm, about 80 nm to about 400 nm, about 100 nm to about 300 nm, about 100 nm to about 200 nm, about 100 nm to about 140 nm, about 50 nm to about 200 nm, about 80 nm to about 160 nm, or about 120 nm. In certain embodiments, the composition of the particles can be varied to create particles as large as about 1 µm, 2 µm, 3 µm, 4 µm, or 5 µm.

The invention also provides a nanoparticle comprising: a) genetic material such as DNA or TNF-α siRNA; b) oleyl trimethyl chitosan (OTMC); c) poly(γ-(4-(((2-(piperidin-1-yl)ethyl)amino)methyl)benzyl-$_L$-glutamate) (PVBLG); d) oleyl-PEG-mannose (OPM); e) oleyl-PEG-cysteamine (OPC); and f) sodium tripolyphosphate (TPP). The nanoparticle can have a diameter of about 80 nm to about 160 nm, or a diameter as described herein.

In some embodiments, the OTMC/PVBLG/siRNA components of the nanoparticle are present in a ratio of about 100:20:1 (w/w). In some embodiments, the OTMC/TPP components of the nanoparticle are present in a ratio of about 8:1 (w/w). In some embodiments, the OTMC/OPM/OPC components of the nanoparticle are present in a ratio of about 1:1:1 (w/w). These components can be varied as described herein.

The invention further provides a pharmaceutical composition comprising a plurality of nanoparticles as described herein in combination with a pharmaceutically acceptable diluent, excipient, or carrier.

The invention further provides methods for orally delivering genetic material such as siRNA to a subject comprising orally administering a plurality of nanoparticles as described herein to a subject, wherein the genetic material (e.g., siRNA) is delivered to cells of the lining of the digestive system of the subject, and the genetic material is transfected into cells of the lining of the digestive system of the subject. In some embodiments, the siRNA is TNF-α siRNA. In certain embodiments, the endogenous production of tumor necrosis factor (TNF)-α in the subject is reduced by at least 50%, at least 60%, at least 70%, at least 80%, at least 90%, or at least 95%, for example, as compared to the absence of the treatment.

In some embodiments, the administration treats or reduces the symptoms of an inflammatory disease. In one embodiment, the inflammatory disease is lipopolysaccharide (LPS)-induced hepatic injury. In other embodiments, the inflammatory disease is ankylosing spondylitis, asthma, atherosclerosis, diabetes, inflammatory bowel disease, joint swelling, ocular inflammation, psoriasis, rheumatoid arthritis, or viral encephalitis.

The invention also provides methods for TNF-α silencing in macrophages in a subject comprising administering to a subject an effective TNF-α silencing amount of a composition comprising a plurality of nanoparticles described herein, wherein the siRNA of the nanoparticles transfects into macrophages of the subject and endogenous production of TNF-α in the subject is reduced by at least 50%, for example, as compared to condition in the absence of administering the particles.

The invention additionally provides pharmaceutical composition for the oral delivery of siRNA comprising a plurality of siRNA-containing nanoparticles, wherein the nanoparticles comprise a) genetic material such as TNF-α siRNA; b) oleyl trimethyl chitosan (OTMC); c) poly(γ-(4-(((2-(piperidin-1-yl)ethyl)amino)methyl)benzyl-$_L$-glutamate) (PVBLG); d) oleyl-PEG-mannose (OPM); e) oleyl-PEG-cysteamine (OPC); and f) sodium tripolyphosphate (TPP). The OTMC/PVBLG/siRNA components of the nanoparticle can be present in a ratio of about 100:20:1 (w/w); the OTMC/TPP components of the nanoparticle can be present in a ratio of about 8:1 (w/w); and the OTMC/OPM/OPC components of the nanoparticle can be present in a ratio of about 1:1:1 (w/w). The ratios can be varies as described herein. The nanoparticle can have a diameter of about 100 nm to about 140 nm, or another diameter or range described herein.

Accordingly, the invention provides the use of a composition comprising the nanoparticles described herein for treating systemic inflammation or a condition caused by local or systemic inflammation.

The invention thus provides novel compositions as described herein, intermediates for the preparation of the compositions, as well as methods of preparing the compositions. The invention provides for the use of the compositions for the manufacture of medicaments useful for the treatment of inflammatory conditions in a mammal, such as a human. The compositions of nanoparticles can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1A:
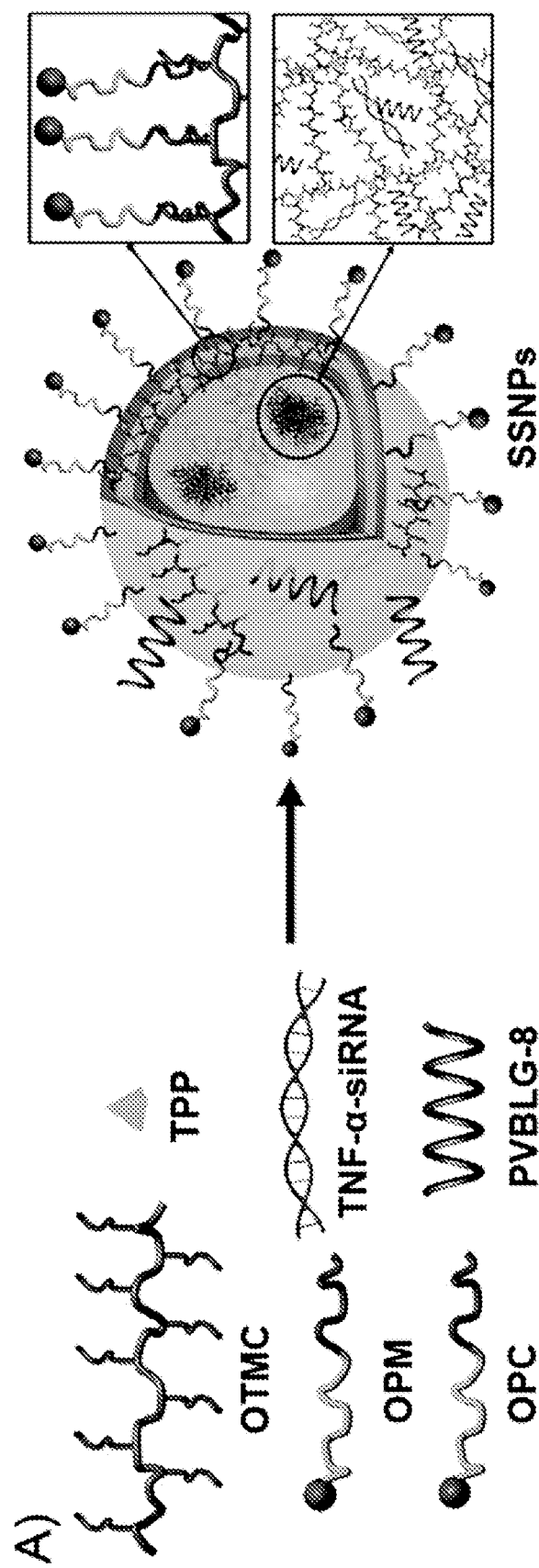
FIG. 1A-C. (A) Schematic illustration of SSNPs and components (sequences disclosed as SEQ ID NOS 1-2, respectively, in order of appearance); (B) SEM image, and (C) particle size and zeta potential of SSNPs (bar =200 nm in SEM image); according to an embodiment.

The invention provides supramolecular self-assembled nanoparticles (SSNPs) that are able to overcome the absorption and transfection barriers posed by intestinal macrophages and exhibit remarkable in vivo oral RNAi efficiency. SSNPs were constructed via the electrostatic and hydrophobic self-assembly of several rationally designed or selected building blocks, including a novel combination of components designed specifically for oral administration of siRNA. Various embodiments of the invention will be further described below.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, group of cells, or production of TNF-α. The inhibition can be greater than about 20%, 40%, 50%, 60%, 80%, 90%, 95%, or 99%, for example, compared to the condition or progression that occurs in the absence of the treatment or contacting.

Supramolecular Self-Assembled Nanoparticle Components.

In one embodiment, the SSNPs comprise a) genetic material; b) a cationic intestinal absorption enhancer; c) a cationic α-helical polypeptide; d) a mannose receptor targeting agent; e) a mucoadhesion agent; and f) a cross-linking agent for stabilizing the nanoparticle. The cationic intestinal absorption enhancer can also act as a transfection reagent. With these building blocks, SSNPs can promote the intestinal absorption of genetic material such as TNF-α siRNA, and therefore facilitate RNAi in macrophages, and thus mediate inflammatory conditions, for example, mediate systemic TNF-α knockdown against lipopolysaccharide (LPS)-induced hepatic injury.

For the construction of SSNPs, (a) genetic material can be condensed with (b) a cationic intestinal absorption enhancer and (c) a cationic α-helical polypeptide via electrostatic interactions. The ratio of (b):(c):(a) can be about 100:20:1 (w/w), while each component can be varied by +/−25% and still form effective nanoparticles. An ionic crosslinker (f) can be used to further stabilize the nanoparticle. An advantageous ratio of (f):(b) can be about 1:8 (w/w), but suitable and effective ratios can be from about 1:4 to about 1:12 or higher, although at low ratios, the particles may increase to larger than 400 nm in diameter. The (d) mannose receptor targeting agent and (e) mucoadhesion agent can be incorporated via intermolecular hydrophobic interactions with the (b) a cationic intestinal absorption enhancer at a ratio of about 1:1:1 (w/w/w)), while each component can be varied by +/−25% and still form effective nanoparticles. Other embodiments have the ratios of (d):(e):(b) by +/−ten-fold for each component, independent of the other components.

Cationic Intestinal Absorption Enhancer. The cationic intestinal absorption enhancer can be trimethyl chitosan (TMC) or a derivative thereof. For example, the cationic intestinal absorption enhancer can be chitosan with the amino group alkylated with one or more other moieties, including ethyl groups, and the like. However derivatives modified to increase lipophilcity can increase the effectiveness of the nanoparticles. One effective modification to conjugate an alkyl chain to available (unalkylated) amino moieties on the TMC, for examples, to form a ($C_{10}$-$C_{24}$) alkyl amide moiety. One specific moiety that if effective is an oleyl moiety. Accordingly, the ($C_{10}$-$C_{24}$)alkyl of the ($C_{10}$-$C_{24}$)alkyl amide moiety can include one or more sites of unsaturation and the ($C_{10}$-$C_{24}$)alkyl can be optionally substituted, cyclic, or branched.

In some embodiments, the cationic intestinal absorption enhancer can be a high molecular mass (~100-300 kDa) chitosan derivative. Various amino groups of the chitosan can be methylated, dimethylated, or trimethylated. Additionally, the chitosans, for example, the trimethyl chitosan, can be covalently modified by conjugation of chitosan amino groups to lipids or fatty acids. The fatty acid moiety can be, for example, the C18 monounsaturated lipid oleic acid, to provide the oleyl-trimethyl-chitosan (OTMC) illustrated below (where n can be about 50 to about 100, about 70 to about 80, or about 77; of course, ammonium, amide, and free amine moieties can occur in random order throughout the OTMC polymer chain; shown as a block below merely for illustration).

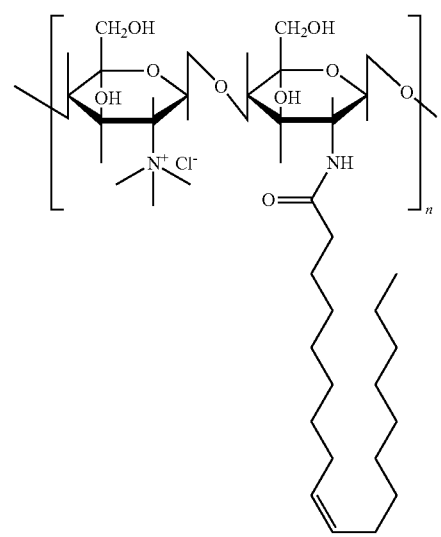

Conjugation of lipid and/or fatty acid groups to amines may be through amide bonds (shown above) or through hydrolysable linkers (e.g., alkyl esters, disulfide bonds, and the like). In one embodiment, lipid groups can be conjugated to one or more units of a chitosan chain through an alkyl ester as illustrated below, where m is 1 to about 12, and $R^x$ is a lipid group, such as a straight chain or branched $C_4$-$C_{30}$(alkyl) group or $C_{10}$-$C_{24}$(alkyl) group, optionally having one, two or three sites of unsaturation. Hydrolysable linkers maybe included on chitosan chains in place of, or in addition to, other lipid chains such as oleoyl groups or other fatty acid chains, for example, as illustrated below.

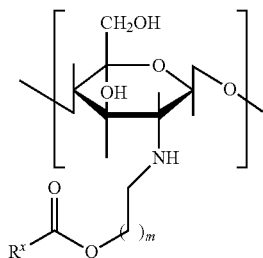

The hydrolysable linker can also be conjugated to the chitosan chain though one or more available hydroxyl moieties of chitosan monomers. Moreover, conjugation to the cationic agent can be via the end groups (one or both) of the chitosan polymer or to any number of interior functional groups, including alcohol or amino groups.

OTMC and derivatives thereof are thus suitable and effective cationic intestinal absorption enhancers. In some embodiments, the OTMC can have a degree of quaternization of about 10% to about 50%, about 20% to about 40%, or about 25% to about 35%. The OTMC can have an oleyl conjugation ratio (percentage of monomers having oleyl groups) of about 5% to about 40%, about 10% to about 30%, or about 15% to about 25%.

Cationic α-Helical Polypeptide. The cationic α-helical polypeptide can be, for example, a polyglutamate wherein the carboxyl moiety of the glutamate side-chains are conjugated with one or more cationic groups. Several suitable and effective α-helical polypeptides are described in US Patent Publication Nos. 2013/0236510 (Cheng et al.) and 2013/0274173 (Cheng et al.). Both polyglutamate and polylysine α-helical polypeptides described therein can be effective cationic α-helical polypeptides. In some embodiments, the cationic α-helical polypeptide can be a poly(γ-(4-vinylbenzyl)-$_L$-glutamate) (PVBLG, e.g., PVBLG-8 illustrated below), or a salt thereof. The number of monomers in the PVBLG can be controlled during synthesis and suitable agents typically include a range of monomers of about 50 to about 300. PVBLG compounds of about 195 or about 200 monomers are highly suitable for use in the nanoparticles described herein.

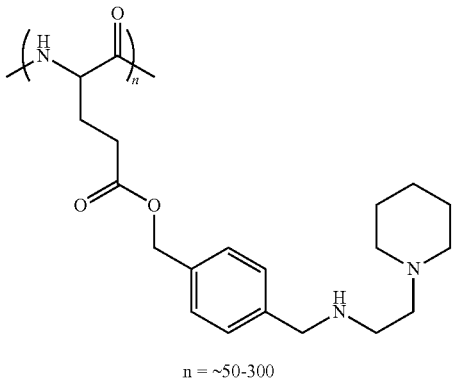

PVBLG-8 n = ~50-300

PVBLG-8 exhibits potent membrane activities and gene delivery efficiencies.

Mannose Receptor Targeting Agent. The mannose receptor targeting agent can include a mannose moiety and a $(C_{10}$-$C_{24})$alkyl moiety linked by poly(ethylene glycol) (PEG). The PEG linker can be any suitable and effective length, such as about 0.5 kDa to about 10 kDa, about 2 kDa to about 6 kDa, or about 3-4 kDa. Incorporating mannose receptor targeting agents such as OPM (see FIG. 1A) enables the nanoparticles to target SSNPs to enterocytes and macrophages that express mannose receptors, thus improving the intestinal absorption and macrophage uptake.

Mucoadhesion Agent. The mucoadhesion agent can include a thiol moiety and a $(C_{10}$-$C_{24})$alkyl moiety linked by poly(ethylene glycol) (PEG). The PEG linker can be any suitable and effective length, such as about 1 kDa to about 10 kDa, about 2 kDa to about 6 kDa, or about 3-4 kDa. Incorporating a mucoadhesion agent such as OPC (see FIG. 1A) improves the mucoadhesion of SSNPs by forming disulfide bonds with mucin glycoproteins enriched in the intestinal mucosa and on cell surfaces.

Crosslinking Agent. In some embodiments, ionic crosslinkers can be included to crosslink the cationic intestinal absorption enhancer and/or cationic α-helical polypeptide and further stabilize the complexes. The addition of ionic crosslinkers can provide focal points to trigger entanglement and crosslinking of the cationic components to increase particle stability. Simultaneously, genetic material such as the short siRNA molecules can therefore be efficiently entrapped inside the nanoparticles.

The ionic cross-linker can be ionic small molecules, ionic large molecules, or mixtures thereof. Examples of ionic small molecules include, for example, sodium tripolyphosphate (TPP), $MgSO_4$, $Na_2SO_4$, and $ZnSO_4$. Examples of ionic large molecules include polysaccharides such as hyaluronic acid or heparin, polypeptides such as poly(γ-glutamic acid). In some embodiments, the cross-linker can be a tripolyphosphate salt, such as sodium tripolyphosphate (TPP), a sulfate salt, such as magnesium sulfate, sodium sulfate, or zinc sulfate, or a combination thereof. Mixtures of ionic small molecules and ionic large molecules may also be employed.

Genetic Material. The nanoparticles can include genetic information, or "genetic material". The phrases "genetic information" and "genetic material" refer to materials found in the nucleus, mitochondria and/or cytoplasm of a cell, which play a fundamental role in determining the structure and nature of cell substances. Genetic material can be a gene, a part of a gene, a group of genes, DNA, RNA, nucleic acid, a nucleic acid fragment, a nucleotide sequence, a polynucleotide, a DNA sequence, a group of DNA molecules, double-stranded RNA (dsRNA), small interfering RNA or small inhibitory RNA (siRNA), microRNA (miRNA), or the genome of an organism. The genetic material can be, for example, any nucleic acid molecule suitable to provide desired coding information to a cell.

In certain embodiments, the genetic material can be DNA (e.g., DNA plasmid pGL3-CV (Promega, Madison, Wis.) containing the firefly luciferase gene under the control of the SV40 promoter) or RNA, such as GFP-siRNA or TNF-α siRNA. The term "genetic material" is intended to encompass any DNA or RNA molecule that has basic research or therapeutic use.

The following paragraphs provide further definitions of genetic material that can be loaded into the nanoparticles described herein.

The terms "nucleic acid" and "polynucleotide" refer to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.*, 19:508 (1991); Ohtsuka et al., *J. Biol. Chem.*, 260:2605 (1985); Rossolini et al., *Mol. Cell. Probes*, 8:91 (1994).

Deoxyribonucleic acid (DNA) in the majority of organisms defines the genetic information while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers.

The terms "nucleic acid", "nucleic acid molecule", "nucleic acid fragment", "nucleic acid sequence or segment," or "polynucleotide" may also be used interchangeably with gene, cDNA, DNA or RNA encoded by a gene, e.g., genomic DNA, and even synthetic DNA sequences. The term also includes sequences that include any of the known base analogs of DNA and RNA. As would be recognized by one of skill in the art, a "nucleic acid fragment" is a portion of a given nucleic acid molecule.

"Messenger RNA" (mRNA) refers to the RNA that is without introns and that can be translated into protein by the cell. "cDNA" refers to a single- or a double-stranded DNA that is complementary to and derived from mRNA. The term "RNA transcript" refers to the product resulting from RNA polymerase catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. A "functional RNA" refers to an antisense RNA, ribozyme, or other RNA that is not translated.

The term "gene" is used broadly to refer to any segment of nucleic acid associated with a biological function. Thus, genes include coding sequences and/or the regulatory sequences required for their expression. For example, a gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The genetic material can be chimeric DNA. The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer. The particles described herein can be used to deliver transgenes to a cell.

A "recombinant DNA" molecule is a combination of DNA sequences that are joined together using recombinant DNA technology and procedures used to join together DNA sequences as described, for example, in Sambrook and Russell, *Molecular Cloning: A Lab Manual*, Cold Spring Harbor, N.Y.: Cold Spring Harbor Laboratory Press (3$^{rd}$ Ed., 2001).

A "vector" is defined to include, inter alia, any plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

An "expression cassette" refers to a DNA sequence capable of directing expression of a particular nucleotide sequence in an appropriate host cell, comprising a promoter operably linked to the nucleotide sequence of interest, which is operably linked to termination signals. It also typically comprises sequences required for proper translation of the nucleotide sequence. The coding region usually codes for a protein of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

The term "siRNA" (short interfering RNA) has the same meaning as typically in the art, i.e., the term refers to short double stranded RNA complex, typically 19-28 base pairs in length. In other words, siRNA is a is double-stranded nucleic acid molecule comprising two nucleotide strands, each strand having about 19 to about 28 nucleotides (i.e. about 19, 20, 21, 22, 23, 24, 25, 26, 27, or 28 nucleotides). The complex often includes a 3'-overhang. SiRNA can be made using techniques known to one skilled in the art and a wide variety of siRNA is commercially available from suppliers such as Integrated DNA Technologies, Inc. (Coralville, Iowa). In one embodiment, a 2'-O-methyl-modified siRNA duplex against TNF-α as described herein can be incorporated into the nanoparticles, wherein the 2'-O-methyl modification on the anti-sense strand eliminates off-target effects, minimizes nonspecific immune responses, and improves siRNA stability.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

A "coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "transfection" and "transformation" refer to the introduction of foreign DNA into eukaryotic or prokaryotic cells, respectively, or the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

The genetic material used in the nanoparticles described herein may be of eukaryotic, prokaryotic, fungal, archaeal or viral origin. The genetic material can be naturally occurring, mutant, or synthetic. The genetic material can include isolated or substantially purified nucleic acids. Naturally occurring nucleotide sequences can be amplified, for example, by polymerase chain reaction (PCR), to obtain suitable quantities for use in the nanoparticles described herein.

The degree of incorporation of genetic material in the nanoparticles can be determined by techniques known in the art including, for example, fluorescence studies, DNA mobility studies, etc., and will vary depending upon desired use. See for example, the techniques described by Hwang and coworkers (Bioconjugate Chem. 2001; 12(2):280-90) and by Liu and coworkers (J. Am. Chem. Soc. 2004; 126 (24):7422-23).

Therapeutic Methods.

Oral administration of SSNPs carrying genetic material such as siRNA can be used to treat a variety of inflammatory conditions including systemic inflammation and associated conditions, including ankylosing spondylitis, asthma, atherosclerosis, diabetes, inflammatory bowel disease, joint swelling, lipopolysaccharide (LPS)-induced hepatic injury, ocular inflammation, psoriasis, rheumatoid arthritis, and viral encephalitis. The intestinal absorption of SSNPs allows for the delivery of the genetic material and can, for example, reduce the production of TNF-α in macrophages. SSNPs can enhanced siRNA transport by 10-30 fold compared to the oral delivery of naked siRNA. Furthermore, as a result of the efficient cellular uptake, SSNPs can inhibited LPS-induced TNF-α production in cells by about 90% at 0.1 μg/mL. For the delivery of genetic material, SSNPs can provide efficacy similar to the Lipofectamine 2000 delivery system while using 10-fold less doses of siRNA.

Thus, orally administered SSNPs can mediate systemic TNF-α knockdown and anti-inflammatory effects, and due to the significant stability of the nanoparticles, the siRNA can be delivered effectively despite the varied pH conditions of the gastric system (pH ~1.2) and the intestinal system (pH ~6.8). Intestinally absorbed SSNPs can infiltrate and transfect macrophages in reticuloendothelial tissues to induce systemic TNF-α knockdown. As a result of systemic TNF-α knockdown, orally delivered SSNPs provide marked anti-inflammatory effects against conditions such as LPS/D-GalN-induced acute hepatic injury. Furthermore, the TNF-α siRNA delivery by SSNPs does not activate pro-inflammatory cytokines or induce IFN-γ responses.

In some embodiments, the nanoparticles are loaded with a therapeutically effective amount of at least one bioactive agent, which bioactive agents can include proteins, peptides, antiviral agents, antineoplastic agents, antibiotics, anti-inflammatory drugs, and the like. Thus, in various embodiments, the nanoparticles can be used to treat not only inflammatory conditions, but also other conditions such as infections and cancer.

Pharmaceutical Formulations

The nanoparticles described herein can be used to prepare therapeutic pharmaceutical compositions, for example, by combining the nanoparticles with a pharmaceutically acceptable diluent, excipient, or carrier. Components of nanoparticles may be added to a composition or carrier system in the form of a salt. For example, in cases where compounds are sufficiently basic or acidic to form stable nontoxic acid or base salts, the nanoparticles may be formed using a salt form of the compound. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The nanoparticles described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes, however the nanoparticles are specifically designed for oral administration.

The nanoparticles described herein may be administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. The nanoparticles may also be combined with one or more excipients and used in the form of ingestible tablets, buccal tablets, troches, capsules, elixirs, suspensions, syrups, wafers, and the like. Such compositions and preparations typically contain at least 0.1 wt. % of the nanoparticles. The amount of nanoparticles as percentage of the composition can vary and may conveniently be from about 0.5% to about 60%, about 1% to about 25%, or about 2% to about 10%, of the weight of a given unit dosage form. The amount of nanoparticles in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The nanoparticles may be administered as a solution or dispersion. Solutions of the nanoparticles can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

A liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride.

Useful liquid carriers include water, alcohols, glycols, or water-alcohol/glycol blends, in which a compound can be dissolved or dispersed at effective levels, optionally with the aid of non-toxic surfactants. Adjuvants such as flavors, fragrances and additional antimicrobial agents can be added to optimize the properties for a given use. Thickeners such as synthetic polymers, fatty acids, fatty acid salts and esters, fatty alcohols, modified celluloses, or modified mineral materials can also be employed with liquid carriers.

Useful dosages of the nanoparticles described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of siRNA or the nanoparticles carrying siRNA required for use in treatment will vary not only with the particular condition being treated and its severity but also with the route of administration, and the age and condition of the patient, and will be ultimately at the discretion of an attendant physician or clinician.

The compound can be conveniently administered in a unit dosage form, for example, containing about 5 µg/kg to about 500 µg/kg, about 10 µg/kg to about 400 µg/kg, about 20 µg/kg to about 200 µg/kg, or about 50 µg/kg to about 100 µg/kg, of siRNA per unit dosage form. Specific unit dosage forms can include about 5 µg/kg, 10 µg/kg, 20 µg/kg, 25 µg/kg, 40 µg/kg, 50 µg/kg, 75 µg/kg, or 100 µg/kg, or siRNA. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating inflammation in a mammal, which involve administering to a mammal having an inflammatory disorder an effective amount of nanoparticles or composition thereof, as described herein. A mammal includes a primate, human, rodent, canine, feline, bovine, ovine, equine, swine, caprine, bovine and the like.

The ability of a compound of the invention to treat inflammation may be determined by using assays well known to the art. For example, the design of treatment protocols, toxicity evaluation, data analysis, and quantification of endogenous TNF-α production are known. In addition, ability of a compound to treat inflammation may be determined using the assays as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials, Cell Culture, and Animal Housing

TNF-α siRNA duplex and negative control siRNA containing scrambled sequences were supplied by Integrated DNA Technologies (Coralville, Iowa, USA) and dissolved in DEPC-treated water before use. The siRNA sequences are shown below in Table A.

TABLE A

Sequence of TNF-α siRNA and Scramble siRNA

| | Sequences |
|---|---|
| TNF-α sense | 5'-GUCUCAGCCUCUUCUCAUUCCUGct-3' (SEQ ID NO: 1) |
| TNF-α antisense | 5'-AGCAGGAAmUGmAGmAAmGAmGGmCUm GAmGAmCmAmU-3' (SEQ ID NO: 2) |
| Scr sense | 5'-UUCUCCGAACGUGUCACGUTT-3' (SEQ ID NO: 3) |
| Scr antisense | 5'-ACGUGACACGUUCGGAGAATT-3' (SEQ ID NO: 4) |

Cy3-labeled TNF-α siRNA duplex (Cy3-siRNA) was used for in vitro cell uptake studies, while DY800-labeled TNF-α siRNA duplex (DY800-siRNA) was used for the in vivo biodistribution study. Chitosan (MW=200 kDa, deacetylation degree of 95%) was purchased from Golden-Shell Biochemical Co., Ltd. (Zhejiang, China). Boc-NH-PEG-succinimidyl valerate (Boc-PEG-SVA, MW=3.4 kDa) was purchased from Laysan Bio (Arab, AL, USA). Dithiothreitol (DTT) was purchased from Roche Diagnostics (Indianapolis, Ind., USA). N-hydroxysuccinimide (NHS), oleoyl chloride, N,N-diisopropyl-ethylamine (DIEA), cystamine dihydrochloride, D-mannosamine hydrochloride, 1,1,3,3-tetramethylguanidine, trifluoroacetic acid, lipopolysaccharide (LPS, from *E. coli* 0111:B4), and D-galactosamine (D-GalN) were purchased from Sigma-Aldrich (St. Louis, Mo., USA) and used as received. Spectra/Por RC dialysis tubing with a molecular weight cut-off (MWCO) of 1 kDa was purchased from Spectrum Laboratories (Rancho Dominguez, Calif., USA). PVBLG-8 was synthesized following previously published procedures (Gabrielson et al., *Angew. Chem. Int. Ed.* 2012, 51, 1143).

Caco-2 cells (human colon carcinoma), Raji B cells (human Burkitt's lymphoma), and RAW 264.7 cells (mouse monocyte macrophage) were purchased from the American Type Culture Collection (Rockville, Md., USA), and cultured in DMEM supplemented with 10% fetal bovine serum (FBS).

Male C57BL/6 mice (8-10 week old) were obtained from Charles River Laboratory (Wilmington, Mass., USA) and were housed in a clean room with four mice per cage. Mice were given access to water ad libitum and exposed to a 12:12 h light-dark cycle at 25±1° C.

Instrumentation.

$^1$H NMR spectra were recorded on a Varian U500 (500 MHz) spectrometer. Electrospray Ionization mass spectrometry (ESI-MS) was performed on a Waters Quattro II Mass Spectrometer. Matrix Assisted Laser Desorption Ionization-Time Of Flight mass spectrometry (MALDI-TOF-MS) was performed on an Applied Biosystems Voyager-DE STR Time of Flight instrument or a Bruker Daltonics UltrafleXtreme MALDI-TOF instrument in positive-ion mode with 2,5-dihydroxybenzoic acid as a matrix. Gel permeation chromatography (GPC) experiments were performed on a system equipped with an isocratic pump (Model 1100, Agilent Technology, Santa Clara, Calif., USA), a DAWN HELEOS multi-angle laser light scattering (MALLS) detector (Wyatt Technology, Santa Barbara, Calif., USA), and an Optilab rEX refractive index detector (Wyatt Technology, Santa Barbara, Calif., USA). The detection wavelength of HELEOS was set at 658 nm. Separations were performed using serially connected size exclusion columns (100 Å, 500 Å, $10^3$ Å and $10^4$ Å Phenogel columns, 5 μm, 300×7.8 mm, Phenomenex, Torrance, Calif., USA) at 60° C. using DMF containing 0.1 M LiBr as the mobile phase. The MALLS detector was calibrated using pure toluene with no need for calibration using polymer standards and can be used for the determination of the absolute molecular weights (MWs). The MWs of polymers were determined based on the do/dc value of each polymer sample calculated offline using the internal calibration system processed by the ASTRA V software (Version 5.1.7.3, Wyatt Technology, Santa Barbara, Calif., USA). Circular dichroism (CD) measurements were carried out on a JASCO J-700 CD spectrometer. The polymer samples were typically prepared at concentrations of 0.02-0.25 mg/mL for CD analysis unless otherwise specified. The solution was placed in a quartz cell with a path length of 0.2 cm and the mean residue molar ellipticity of each polymer was calculated based on the measured apparent ellipticity according to the reported formulas: Ellipticity ([θ] in deg cm$^2$ dmol$^{-1}$)=(millidegrees×mean residue weight)/(path length in millimeters×concentration of polypeptide in mg ml$^{-1}$). The helicity of the polypeptides was calculated using the following equation: helicity=(−[θ$_{222}$]+3,000)/39,000 (Morrow et al., *Biochemistry* 2000, 39, 11657). Lyophilization was performed on a FreeZone lyophilizer (Labconco, Kansas City, Mo., USA).

Example 1

Supramolecular Self-Assembled Nanoparticles (SSNPs)

Figure 1A:
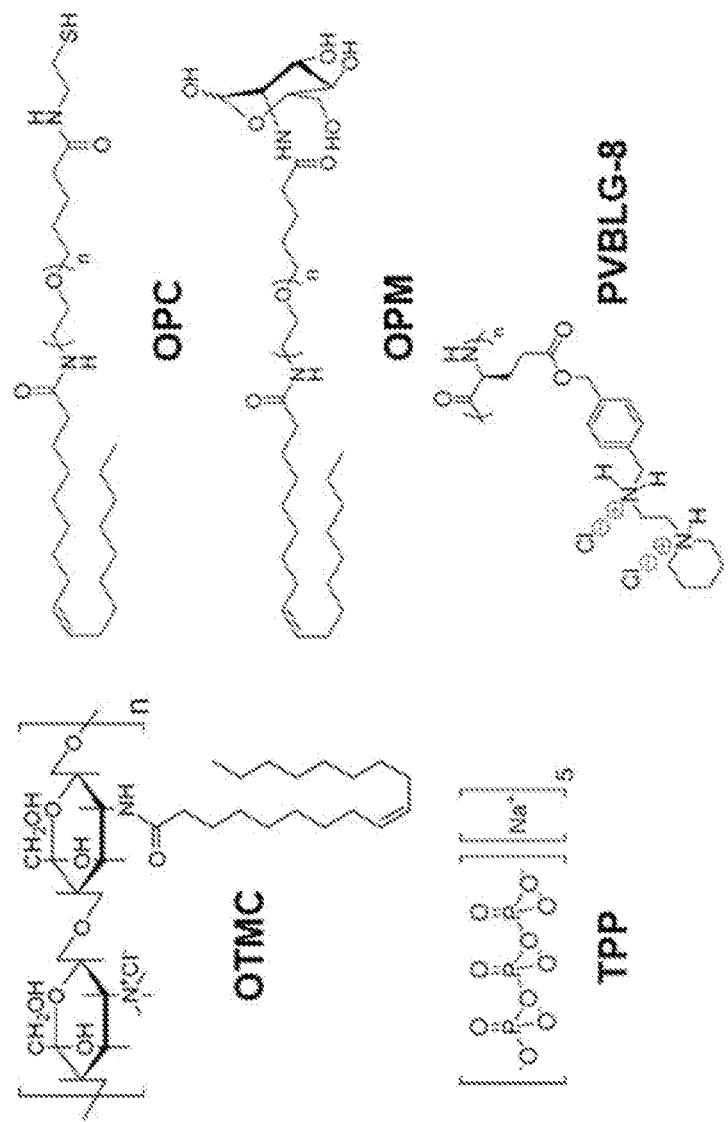
Figures 1B, 1C:
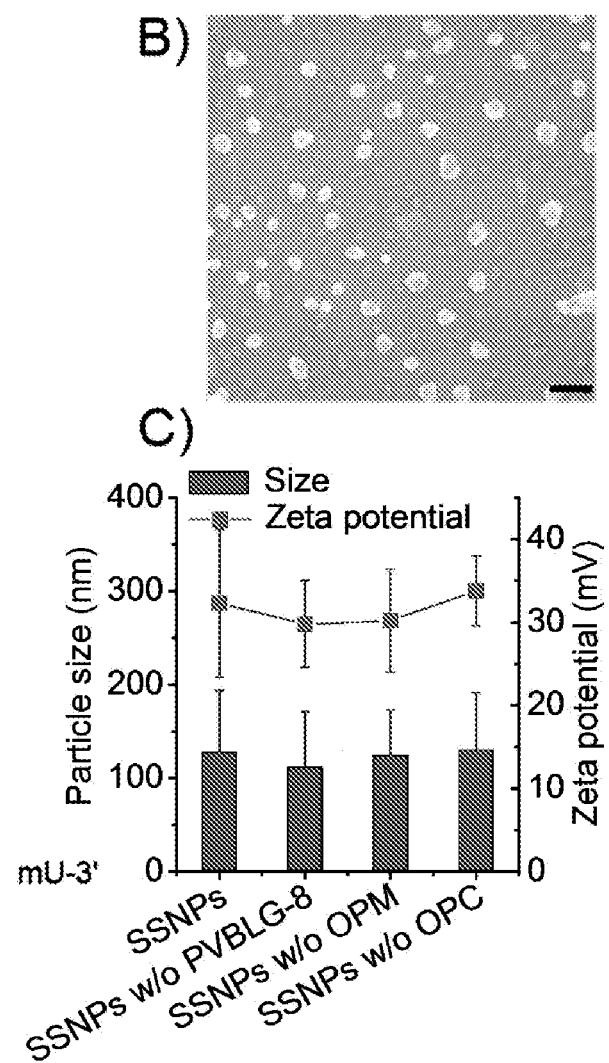

This example describes the design of supramolecular self-assembled nanoparticles (SSNPs) that are able to overcome the absorption and transfection barriers posed by intestinal macrophages and exhibit remarkable in vivo oral RNAi efficiency. SSNPs were constructed via the electrostatic and hydrophobic self-assembly of several rationally designed or selected building blocks, including oleyl trimethyl chitosan (OTMC), poly(γ-(4-(((2-(piperidin-1-yl)ethyl)amino)methyl)benzyl-$_L$-glutamate) (PVBLG-8), oleyl-PEG-mannose (OPM), oleyl-PEG-cysteamine (OPC), sodium tripolyphosphate (TPP), and TNF-α siRNA (FIG. 1).

Trimethyl chitosan (TMC) is as an effective intestinal absorption enhancer as well as transfection reagent. As a more hydrophobic derivative of TMC, OTMC with the oleyl conjugation ratio of about 20% was synthesized and provided further enhanced permeation-enhancing and gene transfection capabilities. PVBLG-8 is a cationic α-helical polypeptide we recently developed (Lu et al., *Nat Commun* 2011, 2, 206; Gabrielson et al., *Angew. Chem. Int. Ed.* 2012, 51, 1143) that exhibits potent membrane activities and gene delivery efficiencies. We incorporated PVBLG-8 (degree of polymerization (DP)=195) into the SSNPs to promote the cellular internalization and endosomal escape. PVBLG-8 adopts super-stable α-helix at a pH of less than 2 to a pH of greater than 9, making it an ideal material for oral delivery applications as it is able to maintain helical secondary structure after passing through both stomach (acidic) and intestinal (weak basic) environments. Incorporating OPM targets SSNPs to enterocytes and macrophages that express mannose receptors, thus improving the intestinal absorption and macrophage uptake. OPC improves the mucoadhesion of SSNPs by forming disulfide bonds with mucin glycoproteins enriched in the intestinal mucosa and on cell surfaces.

OPM and OPC were synthesized by the conjugation methods, as described below, and their structures were confirmed by MALDI-TOF-MS. The 2'-O-methyl-modified siRNA duplex against TNF-α was prepared as reported previously (Howard et al., *Mol Ther* 2009, 17, 162; Amarzguioui et al., *Nat Protoc* 2006, 1, 508), wherein the 2'-O-methyl modification on the anti-sense strand eliminates off-target effects, minimizes nonspecific immune responses, and improves siRNA stability. With the combination of these building blocks, SSNPs promote the intestinal absorption of siRNA (e.g., TNF-α siRNA), facilitate RNAi in macrophages, and thus mediate systemic TNF-α knockdown against lipopolysaccharide (LPS)-induced hepatic injury.

Figure 5:
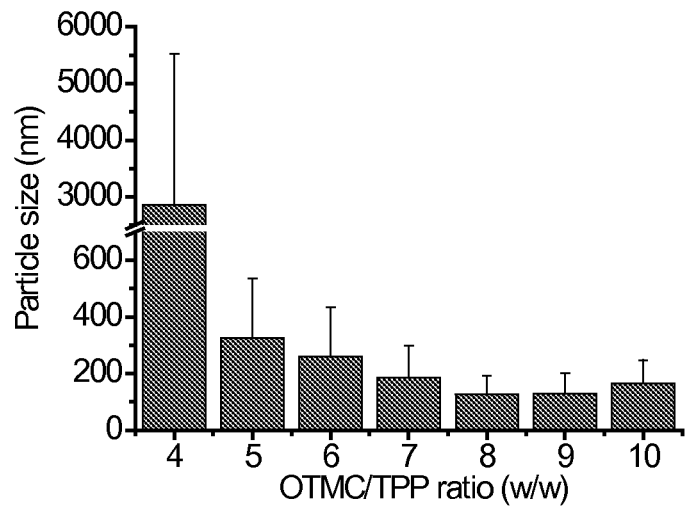
FIG. 5. Size and Zeta potential of SSNPs as a function of OTMC/TPP weight ratios.

For the construction of SSNPs, TNF-α siRNA was condensed with cationic OTMC and PVBLG-8 via electrostatic interactions at the OTMC/PVBLG-8/siRNA ratio of 100:20:1 (w/w). TPP, incorporated at an optimized TPP/OTMC ratio of 1:8 (w/w) (FIG. 5), served as an anionic cross-linker for OTMC to stabilize the complexes. The short length as well as linearity of siRNA can result in weak interaction with polycations (e.g., OTMC and PVBLG-8), which calls for the use of excess amounts of polycations to encapsulate siRNA. For the SSNPs, excess polycations (OTMC and PVBLG-8) were used for effective siRNA encapsulation. The excess amounts of polycations can counteract the competitive siRNA replacement induced by anionic components in physiological fluids. Additionally, excess polycations (especially PVBLG-8 with membrane activity) can strengthen the interaction with oppositely charged cell membranes to enhance the siRNA internalization level.

OPM and OPC were incorporated via intermolecular hydrophobic interactions with OTMC at a fixed ratio of 1:1:1 (w/w/w). The resulting SSNPs had a particle size of 128 nm, zeta potential of 33 mV, and spherical morphology (FIGS. 1B and 1C). siRNA incorporation into the SSNPs was confirmed by a gel retardation assay, which revealed restricted migration of siRNA. When PVBLG-8, OPM, or OPC was removed from SSNPs, particle size and zeta potential remained unchanged (FIG. 1C), allowing comparison of the biological functions of SSNPs with their PVBLG-8-, OPM-, or OPC-depleted analogues.

A. Synthesis of Oleic Acid N-Hydroxysuccinimide Ester (Oleyl-NHS).

NHS (2.67 g, 23.2 mmol) and DIEA (2.72 mL, 15.6 mmol) were dissolved in THF (50 mL). The mixture was cooled in an ice bath to which oleoyl chloride (85%, 6.1 mL, 15.6 mmol) was added dropwise over the course of 1 h. The mixture was allowed to stir at 0° C. for 2 h and then overnight at room temperature. The grey precipitate was removed by centrifugation. After the solvent was removed under vacuum, the resulting yellowish oil was dissolved in DCM (20 mL) and washed with 5% HCl (10 mL×2). DCM was dried over MgSO$_4$ and then evaporated under vacuum to give the crude product. Oleyl-NHS was recrystallized from ethanol (yield 62%). $^1$H NMR (CDCl$_3$, 500 MHz): δ 5.34 (m, 2H, CH=CH), 2.84 (s, 4H, COCH$_2$CH$_2$CO), 2.60 (t, 2H, CH$_2$CH$_2$COON), 2.01 (m, 4H, CH$_2$CH=CHCH$_2$), 1.74 (m, 2H, CH$_2$CH$_2$COON), 1.44-1.24 (m, 20H, other CH$_2$), 0.87 (t, 3H, CH$_3$). ESI-MS (m/z): C$_{22}$H$_{37}$NO$_4$Na (M+Na), calcd., 402.2; found, 402.2.

B. Synthesis and Characterization of Oleyl-Trimethyl Chitosan Chloride (OTMC).

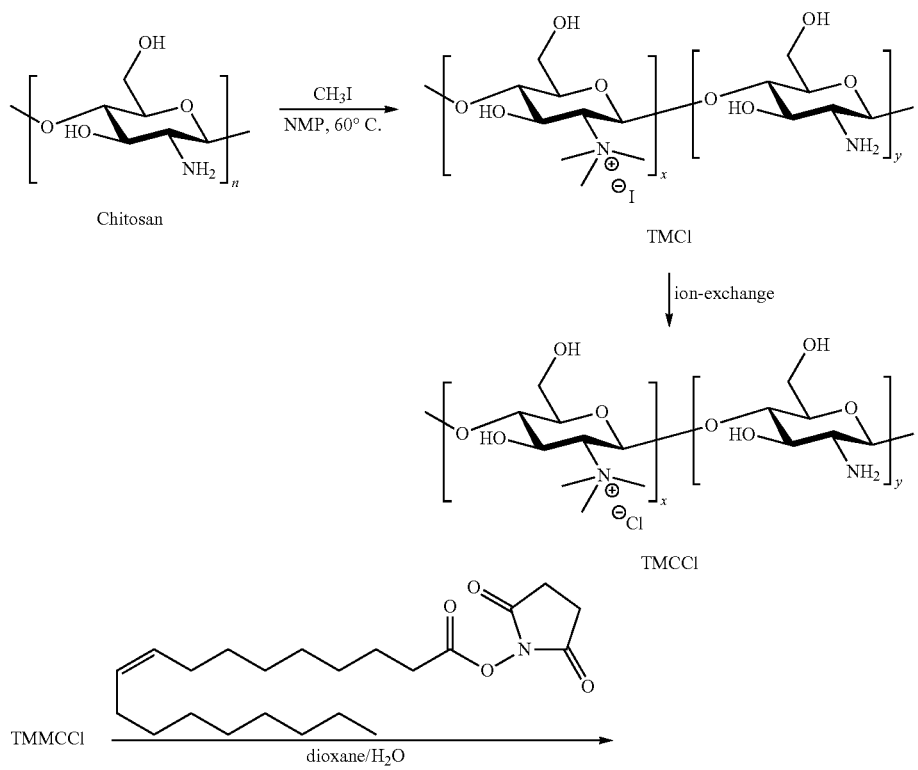

-continued

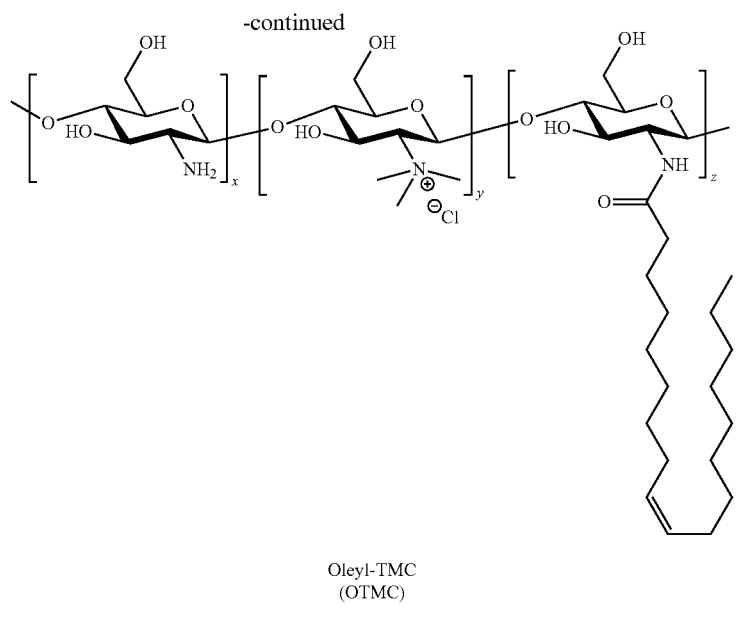

Oleyl-TMC
(OTMC)

Trimethyl chitosan chloride (TMC, MW=200 kDa, quaternization degree of 28.7%) was synthesized as described by Yin and coworkers (*Biomaterials* 2009, 30, 5691). TMC (50 mg, 0.28 mmol of $NH_2$) and oleyl-NHS (10.6 mg, 0.028 mmol) were dissolved in dioxane/water (3 mL, 1:1, v/v), into which DMAP (34.1 mg, 0.28 mmol) and triethylamine (TEA) (80 μL, 0.56 mmol) were added. The solution was stirred overnight at room temperature. The resulting polymer was then precipitated by ethanol/ether/hexane (30 mL, 1:1:1, v/v/v). After being dissolved in water and precipitated by ethanol/ether/hexane (30 mL×3, 1:1:1, v/v/v), the product was dissolved in water and further purified by ultrafiltration (MWCO=10 kDa). $^1H$ NMR was used to characterize the polymers. The quaternization degree was calculated by the integral ratio of trimethyl protons to chitosan backbone C2-C6 protons. The oleyl conjugation degree was calculated by the integral ratio of oleyl methylene protons to trimethyl protons.

C. Synthesis and Characterization of Oleyl-PEG-Mannose (OPM).

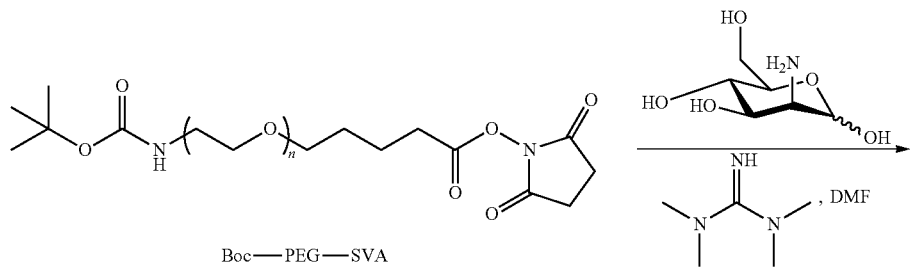

Boc—PEG—SVA

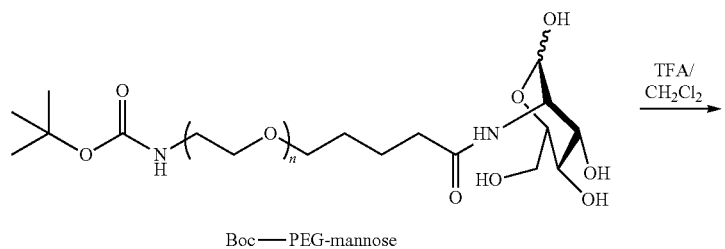

Boc—PEG-mannose

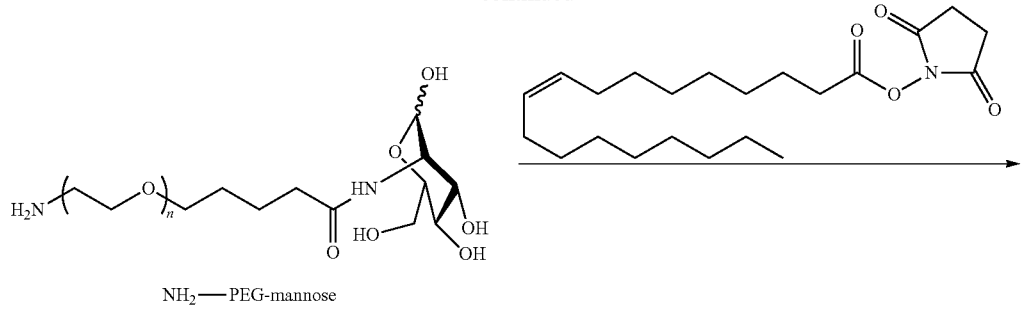

NH₂—PEG-mannose

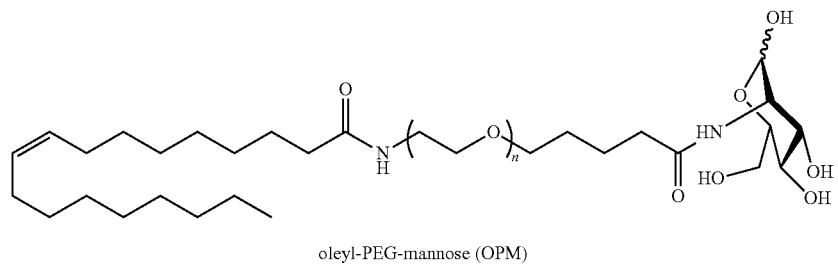

oleyl-PEG-mannose (OPM)

Boc-PEG-mannose was obtained by reacting Boc-PEG-SVA with D-mannosamine in DMF. D-mannosamine hydrochloride (108 mg, 0.50 mmol) and 1,1,3,3-tetramethylguanidine (120 μL, 0.96 mmol) were dissolved in DMF (10 mL). The mixture was then added to a vial containing Boc-PEG-SVA (MW=3.4 kDa, 340 mg, 0.10 mmol). The mixture was stirred for 48 h at 50° C. and dialyzed against DI water for 24 h (MWCO=1 kDa). The product Boc-PEG-mannose was lyophilized (yield 74%) and characterized by MALDI-TOF-MS. Individual peak shifts (relative to Boc-PEG-SVA) corresponding to the deduction of one NHS group and the addition of one mannosamine per PEG were observed (m/z=+64).

Boc-PEG-mannose (250 mg, 0.07 mmol) was deprotected by TFA/DCM (5.0 mL, 1:1, v/v) to yield NH₂-PEG-mannose. The reaction was allowed to proceed for 1 h at room temperature (~22-23° C.). The polymer was then precipitated and washed with cold diethyl ether (20 mL×2, yield 86%). The product (NH₂-PEG-mannose) was characterized by MALDI-TOF-MS. Individual peak shifts (relative to Boc-PEG-mannose) corresponding to the deduction of one Boc group per PEG were observed (m/z=−100).

The final product OPM was synthesized by reacting oleyl-NHS (50.0 mg, 0.13 mmol), DIEA (30 μL, 0.17 mmol) and NH₂-PEG-mannose (200 mg, 0.06 mmol) in 1,4-dioxane/DMF/H₂O (6.0 mL, 4:1:1, v/v/v). The solution was allowed to stir overnight at room temperature, after which it was dialyzed against DI water for 24 h (MWCO=1 kDa). OPM, the final product, was lyophilized (yield 68%) and characterized by MALDI-TOF-MS. Individual peak shifts (relative to NH₂-PEG-mannose) corresponding to the addition of one oleyl group per PEG were observed (m/z=+264).

D. Synthesis and Characterization of Oleyl-PEG-Cysteamine (OPC).

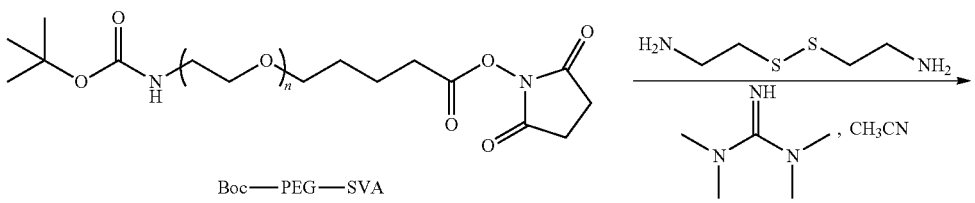

Boc—PEG—SVA

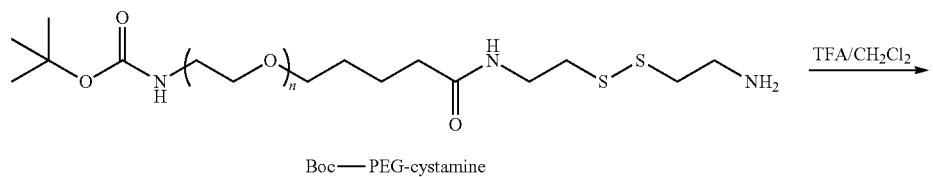

Boc—PEG-cystamine

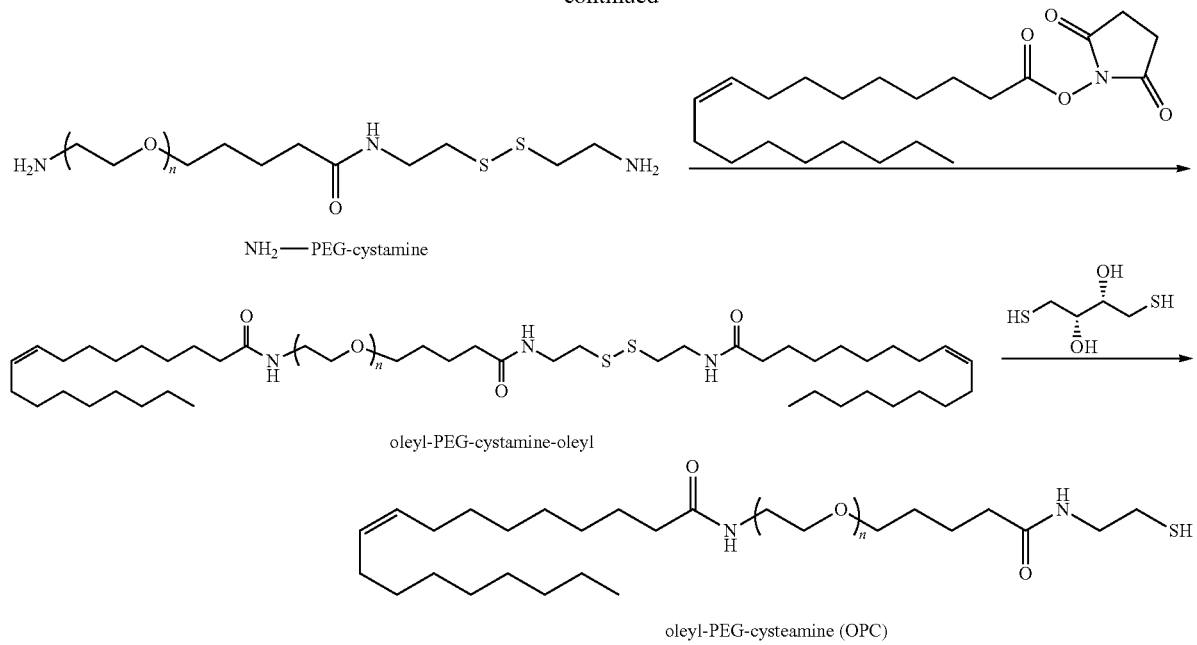

NH₂—PEG-cystamine oleyl-PEG-cystamine-oleyl oleyl-PEG-cysteamine (OPC)

Cystamine dihydrochloride (113 mg, 0.50 mmol) and 1,1,3,3-tetramethylguanidine (120 μL, 0.96 mmol) were dissolved in acetonitrile (10 mL). The solution was then added to a vial containing Boc-PEG-SVA (MW=3.4 kDa, 340 mg, 0.10 mmol). The mixture was stirred overnight at room temperature and dialyzed against DI water for 24 h (MWCO=1 kDa). The product, Boc-PEG-cystamine, was lyophilized (yield 76%) and characterized by MALDI-TOF-MS. Individual peak shifts (relative to Boc-PEG-SVA) corresponding to the deduction of one NHS group and the addition of one cystamine per PEG were observed (m/z=+37).

Boc-PEG-cystamine (250 mg, 0.07 mmol) was deprotected by TFA/DCM (5 mL, 1:1, v/v) to give NH₂-PEG-cystamine. The reaction was allowed to proceed for 1 h at room temperature. The polymer was then precipitated and washed with cold diethyl ether (20 mL×2, yield 90%). The product was characterized by MALDI-TOF-MS. Individual peak shifts (relative to Boc-PEG-cystamine) corresponding to the deduction of one Boc group per PEG were observed (m/z=−100).

Oleyl-PEG-cystamine-oleyl was synthesized by reacting oleyl-NHS (50.0 mg, 0.13 mmol), DIEA (30 μL, 0.17 mmol) and NH₂-PEG-cystamine (200 mg, 0.06 mmol) in 1,4-dioxane/DMF/H₂O (6.0 mL, 4:1:1, v/v/v). The solution was stirred overnight at room temperature and dialyzed against DI water for 24 h (MWCO=1 kDa). The product, Oleyl-PEG-cystamine-oleyl, was lyophilized (yield 72%) and characterized by MALDI-TOF-MS. Individual peak shifts (relative to NH₂-PEG-cystamine) corresponding to the addition of two oleyl groups per PEG were observed (m/z=+529).

The final product OPC was obtained by reacting oleyl-PEG-cystamine-oleyl (200 mg, 0.05 mmol) and DTT (11.0 mg, 0.07 mmol) in DI water (6.0 mL). The reaction was allowed to proceed overnight at room temperature and then dialyzed against DI water (MWCO=1 kDa). The product was lyophilized (yield 82%) and characterized by MALDI-TOF-MS. Individual peak shifts (relative to oleyl-PEG-cystamine-oleyl) corresponding to the deduction of one (2-oleamidoethyl)thio group per PEG were observed (m/z=−340).

E. Preparation and Characterization of SSNPs.

siRNA and sodium tripolyphosphate (TPP) were dissolved in DEPC-treated water at 0.2 mg/mL and 1 mg/mL, respectively, and then mixed at the siRNA/TPP weight ratio of 1:12.5. OTMC, PVBLG-8, OPM, and OPC were separately dissolved in DEPC-treated water at 2 mg/mL, 1 mg/mL, 10 mg/mL, and 10 mg/mL, respectively and then mixed at the predetermined weight ratios of 5:1:5:5. Subsequently, the OTMC/PVBLG-8/OPM/OPC mixture was added to siRNA/TPP at the OTMC/TPP weight ratio of 8:1 followed by vortexing for 30 seconds and incubation at 37° C. for 30 minutes. The obtained SSNPs were characterized for size and zeta potential using dynamic light scattering (DLS, Zetasizer Nano-ZS, Malvern). A gel retardation assay was used to evaluate siRNA condensation. Briefly, SSNPs or naked siRNA were loaded in 4% low-melting agarose gel followed by electrophoresis at 56 V for 1 hour and visualization of siRNA migration by gel documentation. SSNPs were also characterized by SEM (4800, Hitachi, Japan). The stability of SSNPs against pH alteration, salt, and dilution was evaluated in terms of particle size and zeta potential. In order to evaluate the stability of SSNPs against salt and dilution, they were diluted with PBS (0.15 M, pH 6.8) up to 100-fold. To simulate the pH alteration in the gastrointestinal tract, the pH of the SSNPs suspension was adjusted to 1.2 using 1 N HCl and back to 6.8 using 1 N NaOH.

Stability of siRNA. To evaluate the in vivo stability of siRNA following oral administration, siRNA-containing SSNPs or naked siRNA were treated with mouse serum or intestinal fluids. Blood was collected from the orbital sinus of male C57BL/6 mice and centrifuged at 12,000 rpm for 4 minutes to separate the serum. To prepare the intestinal fluids, mice were sacrificed and the whole small intestine was washed with cold PBS (2 mL, 0.2 M, pH 7.4) through insertion of a sonde needle into the upper side and cannulation on the lower side. The washed solution was centrifuged at 12,000 rpm and 4° C. for 20 minutes, and the supernatant was collected as the intestinal fluids. SSNPs (0.2 mL) were mixed with mouse serum or intestinal fluids (0.2 mL). After incubation at 37° C. for 2 hours, the mixture was heated at 80° C. for 5 minutes to deactivate the nucleases. Heparin (1000 U/mL) was added to dissociate the siRNA. The mixture was loaded on 4% agarose gel followed by electrophoresis at 56 V for 1 hour and siRNA integrity visualization by gel documentation.

Mucoadhesion. SSNPs (400 µL) were mixed with mucin solution (1 mL, 200 µg/mL) and incubated at 37° C. for 8 hours. The solution was centrifuged at 12,000 rpm for 10 minutes. The mucin adsorption level was determined by harvesting the supernatant and measuring the remaining mucin content with a colorimetric method using periodic acid/Schiff staining (He et al., *Int J Pharmaceut* 1998, 166, 75).

Example 2

Intestinal Absorption and Permeation of SSNPs

Figure 2:
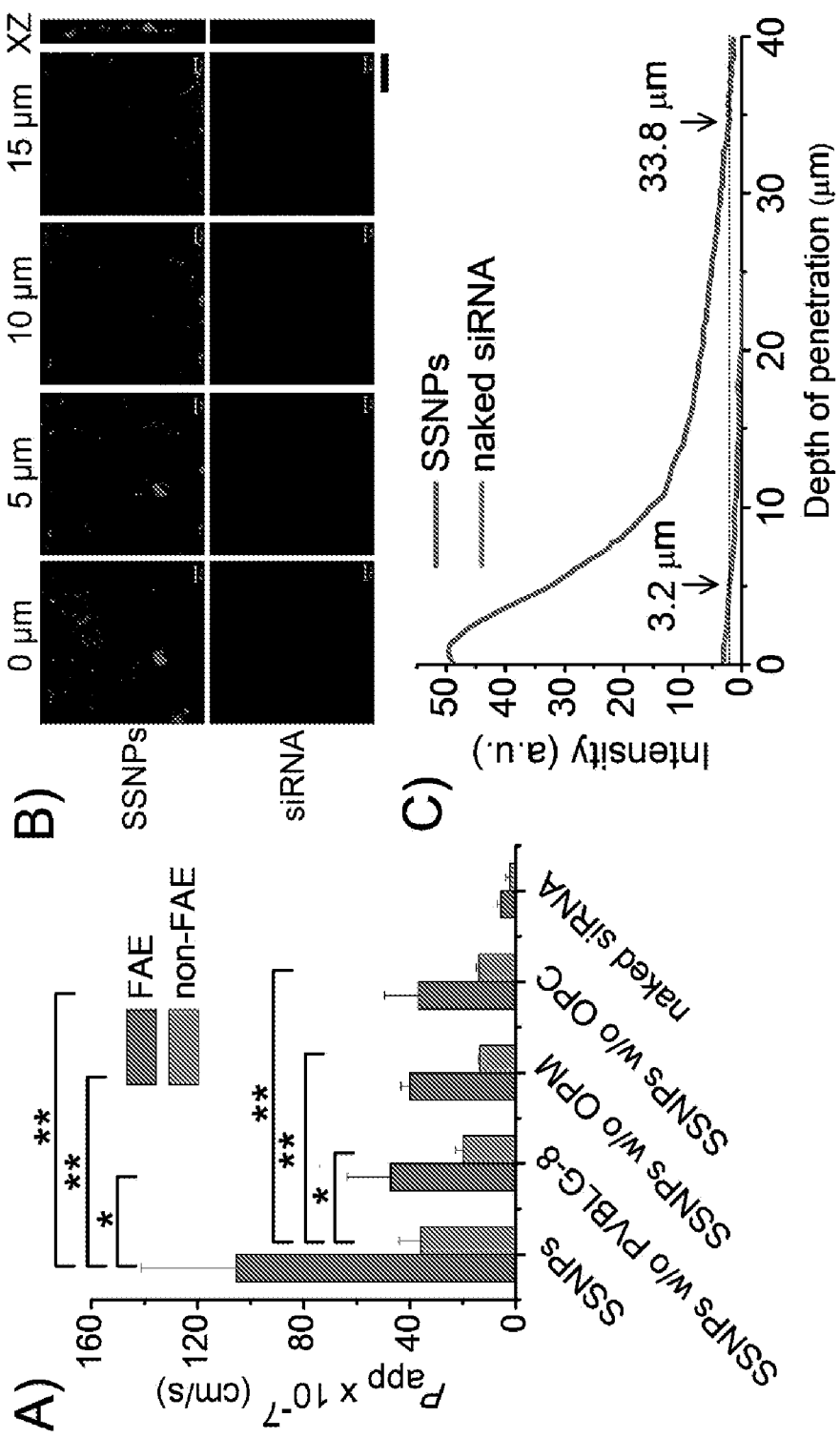
FIG. 2A-G. Intestinal absorption of Cy3-siRNA-containing SSNPs. (A) $P_{app}$ of Cy3-siRNA across human non-FAE (left column) and FAE models (right column) (n =3). (B) CLSM images showing cross-sections of the FAE model at 5-µm increments in the Z direction following SSNPs treatment for 4 h (bar =20µm). (C) Penetration depth of Cy3-siRNA (upper line) in the FAE model compared to naked siRNA (lower line). (D) TEER of the FAE model following incubation with SSNPs (n =3); SSNP data are shown on the line indicated with squares (lowest value at each time increment); similar data was obtained using a non-FAE model. (E) CLSM images of the FAE model stained for ZO-1 after treatment with SSNPs (bar =20 µm). (F) Uptake of SSNPs in the non-FAE model following 4 hour incubation (n =3). (G) Intestinal absorption pathways of SSNPs, including transcellular transport by M cells (pathway I), uptake by normal enterocytes (pathway II), and paracellular transport via transiently opened tight junctions (pathway III). The absorbed SSNPs were transferred either to GAMs or to systemic circulation.
Figure 2:
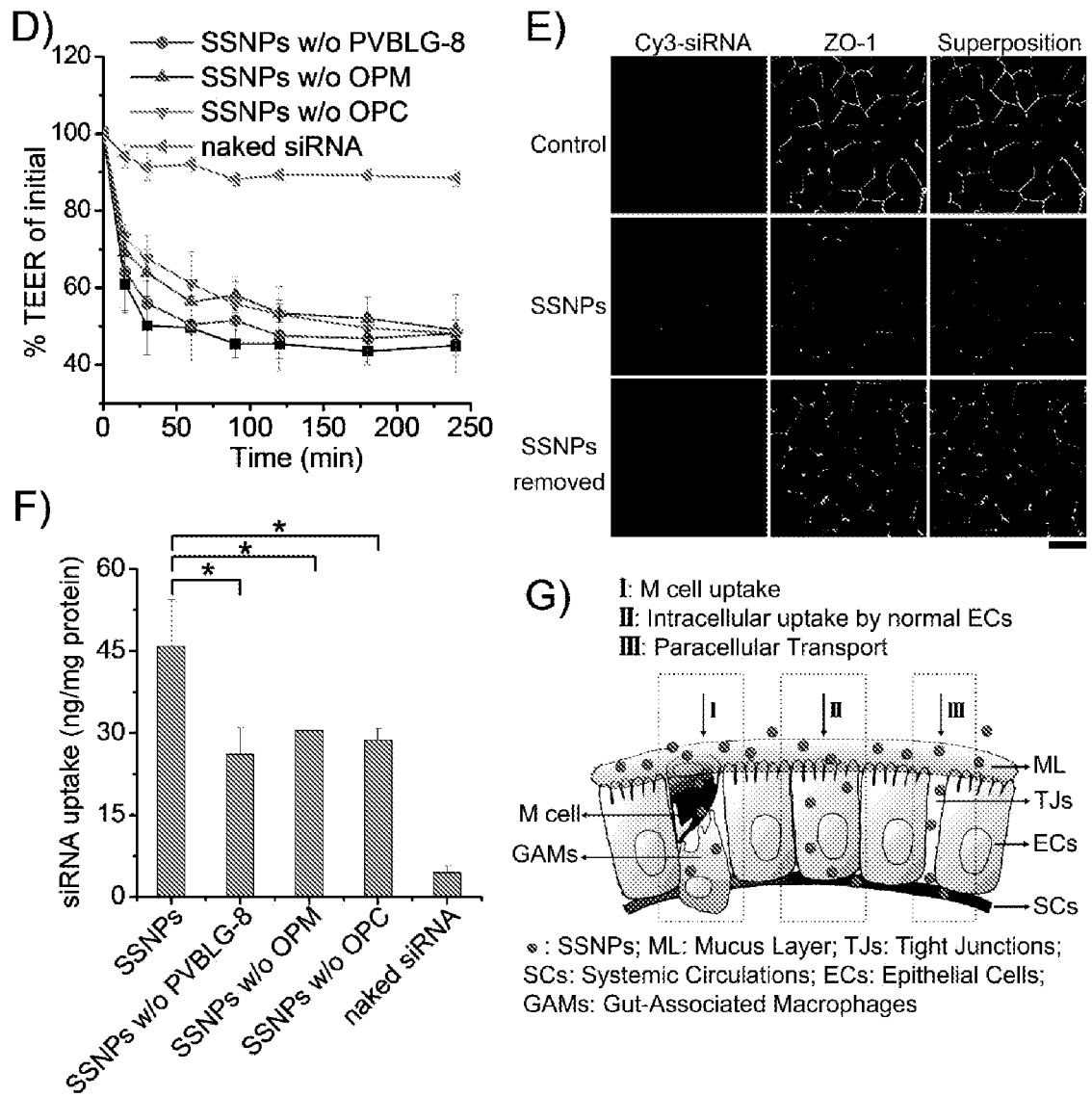

The intestinal absorption of SSNPs and the associated mechanisms were examined in two in vitro models. The non-follicle-associated epithelia (non-FAE) model, obtained from monocultured Caco-2 cell monolayers, has been widely used as an in vitro intestinal epithelia model because the cultured Caco-2 cells differentiate into polarized, columnar cells and transporting epithelium with well-developed microvilli. The FAE model, obtained from Caco-2 cell monolayers co-cultured with Raji B lymphocytes, additionally contains a distinctive M cell phenotype. We monitored the apparent permeability coefficient ($P_{app}$) of Cy3-siRNA in these two models which represented the intestinal transport level. SSNPs enhanced siRNA transport in both models by 15-18 fold (FIG. 2A), which accorded well with their deeper penetration into the cell monolayers (FIG. 2B). In FIG. 2B, evidence of Cy3-siRNA can be observed at 0 µm, 5 µm, 10 µm, and 15 µm for the SSNPs, while evidence Cy3-siRNA can barely be detected at 0 µm and 5 µm, and not at all at 10 µm, and 15 µm for the naked siRNA.

Quantitative analysis of the images confirmed an increased siRNA penetration depth from 3.2 µm (naked siRNA) to 33.8 µm (SSNPs) (FIG. 2C). We further noted 2.9-fold increment of siRNA transport in the FAE-model compared to that in the non-FAE model for SSNPs (FIG. 2A), indicating that a large proportion of the SSNPs were absorbed via transcellular uptake by M cells (pathway I, FIG. 2G), the most rapid and potent translocation pathway during intestinal absorption.

In addition to M cell uptake, we also evaluated the involvement of two other pathways, intracellular uptake by normal enterocytes (pathway II, FIG. 2G) and paracellular transport via tight junctions (TJs, pathway III, FIG. 2G). As shown in FIG. 2D, addition of the SSNPs at the apical side of the monolayers rapidly decreased the transepithelial electric resistance (TEER) values, indicating that SSNPs opened the TJs to facilitate paracellular siRNA transport. The underlying mechanisms were explored by immunostaining the TJ-associated proteins (TJAPs), F-actin and ZO-1. Untreated cell monolayers showed uniformly distributed F-actin and continuous cell frame distribution of ZO-1 proteins (control, FIG. 2E).

Figure 6:
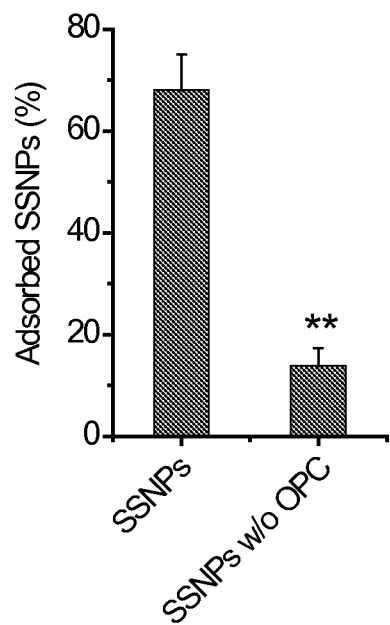
FIG. 6. Mucoadhesion of SSNPs as determined by the mucin adsorption assay. **p<0.01 v.s. SSNPs.

Upon treatment of SSNPs, F-actin filaments were redistributed, shortened, and aggregated, and ZO-1 proteins appeared to be loosened and discontinuous (SSNPs), indicating that the SSNPs triggered the reconfiguration of TJAPs and opened the TJs. After removal of SSNPs and further incubation for 24 hours, the ZO-1 and F-actin patterns recovered to the untreated state (control), indicating reversible opening and restoration of epithelial TJs. In the non-FAE model containing only normal enterocytes, SSNPs markedly promoted the uptake of Cy3-siRNA (FIG. 2F), indicating that SSNPs enhanced the transcellular uptake of siRNA by normal enterocytes. In these experiments, we noted significantly decreased siRNA transport and uptake in both models when PVBLG-8, OPM, or OPC were removed from the SSNPs (FIG. 2A and FIG. 2F). This observation shows that intestinal absorption of siRNA can be improved by OPM-mediated targeting of SSNPs to enterocytes and M cells, OPC-mediated intestinal mucoadhesion (FIG. 6), and PVBLG-8-mediated membrane permeation.

Permeation Studies in Human FAE and Non-FAE Models. To establish the human non-FAE model, Caco-2 cells were seeded on Millicell® (pore size 0.4 µm, surface area 0.6 cm$^2$, Millipore) at 5×10$^4$ cells/well and subsequently cultured for 21 days to form monolayers (Kerneis et al., *Science* 1997, 277, 949). The media at both the apical (AP) and basolateral (BL) sides were replaced daily. The transepithelial electric resistance (TEER) values of monolayers reached 300-350 Ω/cm$^2$ after the 21-day culture.

To establish the FAE model, Caco-2 cells were cultured on Millicell® for 16 days before Raji B cells were seeded on the BL side at 5×10$^4$ cells/well. The cells were co-cultured for another 7 days with media at the AP side being replaced daily. The TEER values of the co-cultured monolayers were similar to the mono-cultured cell monolayers (300-350 Ω/cm$^2$), indicating that the introduction of Raji cells did not alter the polarity of Caco-2 cells and the intercellular tight junctions.

Cy3-siRNA containing SSNPs or naked Cy3-siRNA was added to the AP side of the FAE and non-FAE models in HBSS at 0.4 µg Cy3-siRNA/well. At selected time intervals, transepithelial electrical resistance (TEER) was measured and an aliquot of 50 µL was withdrawn from the BL side to quantify transported Cy3-siRNA. The apparent permeability coefficient ($P_{app}$) for Cy3-siRNA was calculated using the equation of $P_{app}=Q/Act$, where Q is the total amount of Cy3-siRNA permeated (ng), A is the diffusion area of the cell monolayers (cm$^2$), c is the initial concentration of Cy3-siRNA on the AP side (ng/cm$^3$), and t is the total time of the transport experiment(s).

After the 4 hour transport study, Cy3-siRNA penetration/distribution in the cell monolayers was observed by CLSM (LSM 700, Zeiss, Germany) at optical sections with 5-µm in increment. The fluorescence intensity in each section was analyzed by Image J. To quantify the penetration of SSNPs, we defined the penetration depth as the distance from the periphery of the AP side to the site where the fluorescence intensity decreased by 95% as compared to the maximal fluorescent intensity of the SSNPs-treated cell monolayers at the apical periphery. The uptake level of Cy3-siRNA in the cell monolayers was also determined by lysing the monolayers with RIPA lysis buffer (500 µL) and quantifying the Cy3-siRNA content in the lysate. Results were expressed as ng of Cy3-siRNA per mg of cellular protein.

The tight junction protein-associated transport mechanism was evaluated by immunostaining. After treatment of cell monolayers with SSNPs for 4 hours, cells were fixed in 3.7% paraformaldehyde, washed with PBS for three times, and permeabilized with 0.2% Triton X-100 for 15 minutes at 37° C. Cells were then washed with PBS and blocked with 1% bovine serum albumin (BSA) for 60 minutes at 37° C. Subsequently, the cells were treated with mouse monoclonal anti-ZO-1-Alexa Fluor® 488 (Invitrogen, Grand Island, N.Y., USA) at 1:50 dilution for 60 minutes at 37° C. or with phalloidin-Alexa Fluor® 350 (Invitrogen, Grand Island, N.Y., USA) at 4° C. for 20 minutes. The stained cells were evenly mounted on slides and analyzed by using CLSM.

Example 3

Intracellular Delivery and RNAi Efficiency of SSNPs

Figure 3:
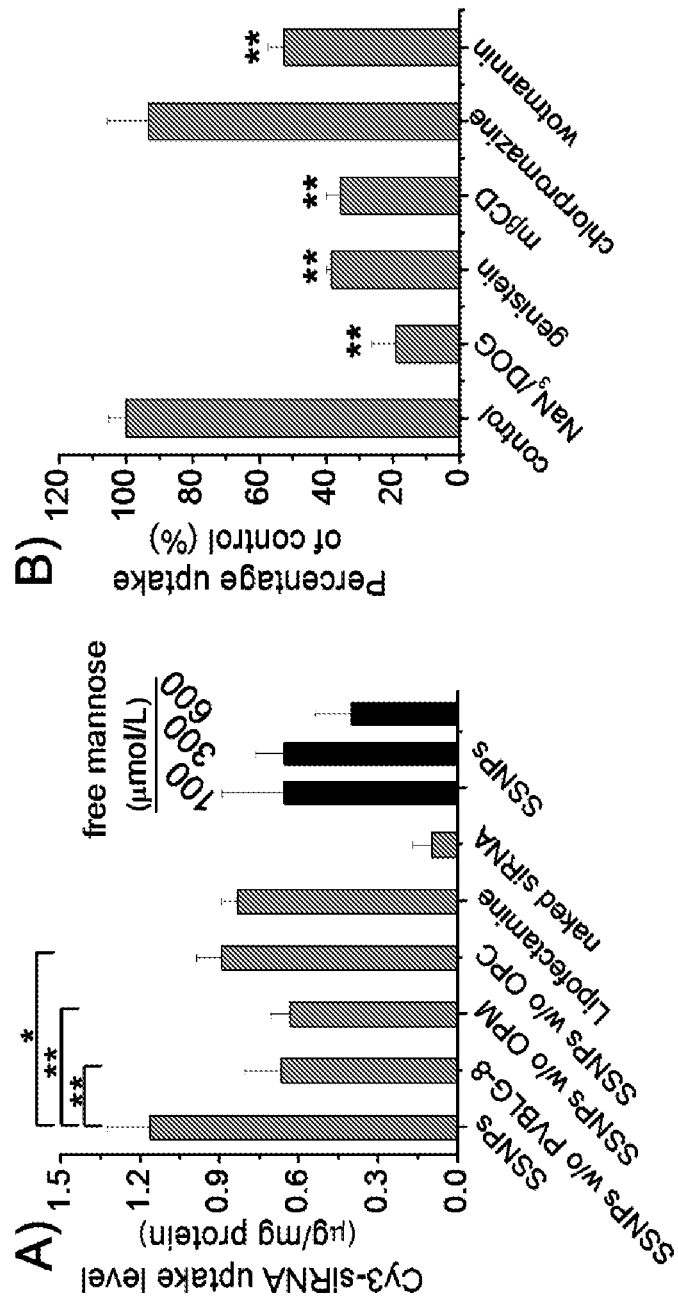
FIG. 3A-H. SSNPs deliver TNF-α siRNA to macrophages via mannose receptor-mediated endocytosis and attenuate TNF-α production in vitro. (A) Uptake of Cy3-siRNAcontaining SSNPs in RAW 264.7 cells following incubation for 4 hours (n =3). (B) Uptake of SSNPs in RAW 264.7 cells in the presence of various endocytosis inhibitors (n =3). (C) CLSM images showing internalization of Cy3-siRNA-containing SSNPs in RAW 264.7 cells. Cy3-siRNA-SSNPs co-localized with FITC-CTB (D, white arrows) rather than with transferring-Alexa Fluor 635 (E) (bar =10 μm). TNF-α (F) and TNF-α mRNA levels (G) of RAW 264.7 cells following treatment with SSNPs at 0.1 μg siRNA/mL. (H) Comparison on the TNF-α knockdown efficiencies of SSNPs and LPF2000/siRNA complexes at various siRNA doses (n =3).
Figure 3:
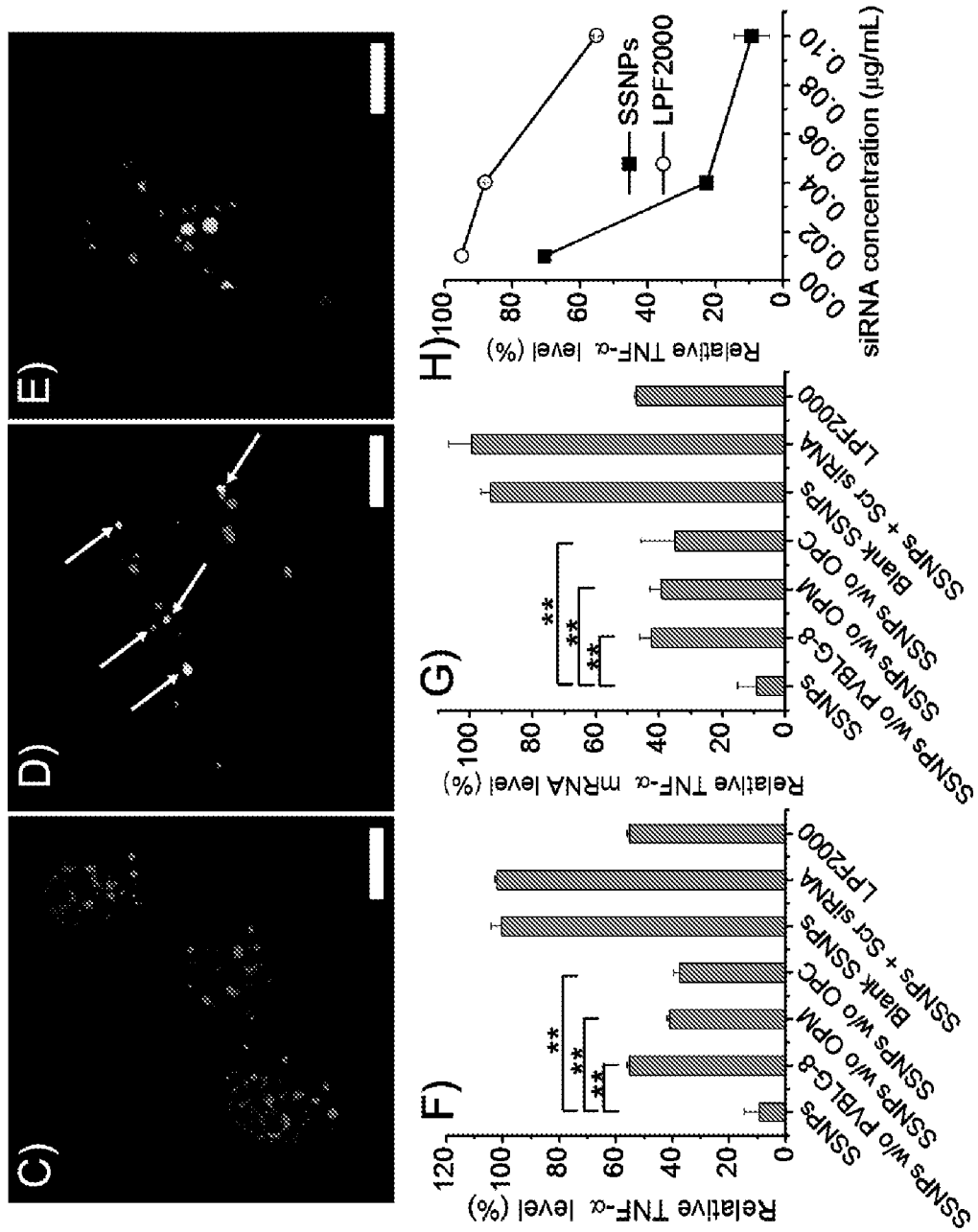

Because macrophages are the target cells for TNF-α siRNA-mediated gene silencing, we explored the intracellular delivery and RNAi efficiency of SSNPs in RAW 264.7 cells. SSNPs markedly increased Cy3-siRNA uptake levels (FIG. 3A), and internalized Cy3-siRNA was observed in the cytoplasm (FIG. 3C). When PVBLG-8, OPM, or OPC was removed from SSNPs, the siRNA uptake level was significantly reduced, supporting our design strategy of enhancing macrophage uptake via PVBLG-8-mediated membrane penetration, OPM-mediated mannose-receptor recognition, and OPC-mediated cell binding.

The mannose-receptor mediated targeting effect was further verified by the reduced siRNA uptake level when free mannose was added to competitively occupy the mannose receptors (FIG. 3A). Because RNAi efficiency is closely related to the intracellular kinetics, we also probed the internalization pathways of SSNPs using various endocytic inhibitors. NaN$_3$/deoxyglucose (DOG) substantially reduced the uptake of SSNPs, indicating that they were mainly internalized via energy-dependent endocytosis (FIG. 3B). The caveolae inhibitors methylated-β-cyclodextrin (mβCD) and genistein and macropinocytosis inhibitor wortmannin significantly suppressed SSNPs uptake, indicating that both caveolae and macropinocytosis were involved in endocytosis. In contrast, chlorpromazine exerted unappreciable inhibitory effect, suggesting irrelevance to clathrin-mediated endocytosis.

For further validation, we co-incubated Cy3-siRNA-containing SSNPs with transferrin-Alexa Fluor 635 or FITC-cholera toxin B (FITC-CTB), which are endocytosed via clathrin- and caveolae-mediated pathways, respectively. CLSM analysis showed that internalized SSNPs co-localized with CTB (FIG. 3E) rather than with transferrin (FIG. 3D), which confirmed the caveolae pathway for SSNPs uptake. As a result of the efficient cellular uptake, SSNPs inhibited LPS-induced TNF-α production in RAW 264.7 cells by ~90% at 0.1 μg/mL (FIGS. 3F and 3G). In agreement with the decreased uptake level, omission of PVBLG-8, OPM, or OPC from SSNPs resulted in a significant decrease in TNF-α knockdown efficiency. More noteworthy, SSNPs markedly outperformed Lipofectamine 2000 (LPF2000), exhibiting similar efficacy at a siRNA dose 10-fold less than LPF2000 (FIG. 3H) and 20~100-fold less than other non-viral vectors.

Cell Uptake Analysis. RAW 264.7 cells were seeded on 24-well plates at 5×10$^4$ cells/well and cultured for 24 hours. The medium was replaced by serum-free DMEM (500 μL), and Cy3-siRNA-containing SSNPs were added (0.4 μg siRNA/well) before incubation at 37° C. for 4 hours. Cells were washed with PBS three times and then lysed with the RIPA lysis buffer (500 μL). The quantity of Cy3-siRNA in the lysate was determined by spectrofluorimetry ($\lambda_{ex}$=480 nm, $\lambda_{em}$=520 nm); the total protein content was determined by BCA assay. Uptake level was expressed as the amount of Cy3-siRNA per mg of cellular protein. In order to elucidate the effect of mannose-receptor recognition during nanoparticle internalization, cell uptake study was performed in serum-free DMEM supplemented with 100, 300, and 600 μmol/L of mannose, respectively. Internalization and intracellular distribution of Cy3-siRNA in RAW 264.7 cells was also visualized by CLSM (700, Zeiss, Germany) following nanoparticle treatment, fixation with 4% paraformaldehyde (PFA), and nuclei-staining with DAPI.

To explore the mechanisms involved in the uptake process, cells were pre-incubated with endocytic inhibitors including NaN$_3$ (200 mM)/deoxyglucose (50 mM), chlorpromazine (10 μg/mL), genistein (200 μg/mL), methyl-β-cyclodextrin (mβCD, 50 μM), and wortmannin (50 nM) for 30 minutes prior to nanoparticle application and throughout the 4 hour uptake experiment at 37° C. Results were expressed as percentage uptake of the control where cells were incubated with SSNPs at 37° C. for 4 hours. To further explore the caveolae-mediated endocytosis, RAW 264.7 cells were incubated with Cy3-siRNA-containing SSNPs and FITC-CTB (5 μg/mL) for 2 hours before CLSM observation. To evaluate the clathrin-mediated pathway, RAW 264.7 cells were incubated with Cy3-siRNA-containing SSNPs and transferrin-Alexa Fluoro 635 (10 μg/mL) for 2 hours before the analysis by CLSM.

In Vitro TNF-α Knockdown in Macrophages. RAW 264.7 cells were seeded on 24-well plates at 5×10$^4$ cells/well and cultured for 24 hours. The medium was changed to serum-free DMEM and siRNA-containing SSNPs were added at pre-determined siRNA concentrations. Following incubation for 4 hours, the medium was replaced with serum-containing DMEM and cells were further cultured for 20 hours before LPS stimulation (100 ng·mL$^{-1}$) for 3 hours. Extracellular TNF-α production was quantified by ELISA (R&D Systems, MN, USA). The TNF-α mRNA level was monitored by real-time PCR. The silencing efficiency was denoted as the percentage of TNF-α or TNF-α mRNA levels of the control cells which did not receive nanoparticle treatment. To prepare samples for real-time PCR analysis, RNA was isolated from cells using Trizol reagent (Invitrogen). cDNA was synthesized from 500-ng total RNA using the high capacity cDNA reverse transcription kit (Applied Biosystems, Carlsbad, Calif., USA) according to the manufacturer's suggested protocol. Synthesized cDNA, TNF-α primers (forward and reverse, Table B), and SYBR Premix Ex Taq™ were mixed and run on the ABI PRISM 7900HT Real-Time PCR system (Applied Biosystems, Carlsbad, Calif., USA). Sequences of the primers used were designed with Primer Bank. The ribosomal mRNA actin was used as an internal loading control, and its expression did not change over the 24 hour period following addition of LPS, SSNPs, or siRNA.

TABLE B

Forward (F) and Reverse (R) TNF-α primer sequences.

| Primer | Sequence |
| --- | --- |
| TNF-α F | CCACCACGCTCTTTCTGTCTACTG (SEQ ID NO: 5) |
| TNF-α R | GGGCTACAGGCTTGTCACTCG (SEQ ID NO: 6) |

Cytotoxicity of SSNPs. Caco-2 and RAW 264.7 cells were seeded on 96-well plates at 1×10$^4$ cells/well and cultured for 24 hours before media replacement with serum-free DMEM (100 μL/well). SSNPs were added at final siRNA concentrations of 0.05, 0.1, 0.2, 0.5, and 1 µg/well. Following incubation for 4 hours, the medium was removed and serum-containing DMEM was added. Cells were further cultured for 20 hours before viability assessment by the MTT assay.

Example 4

SSNPs for Mediation of Systemic TNF-α Knockdown and Anti-Inflammatory Effects

The ability of orally administered SSNPs to mediate systemic TNF-α knockdown and anti-inflammatory effect was evaluated in LPS/D-GalN-induced murine hepatic injury model. The stability of SSNPs was first evaluated under simulated conditions. To mimic the pH change in the GI tract, the pH of SSNPs was adjusted from 6.8 (intestinal pH) to 1.2 (gastric pH) and then back to 6.8. Size and zeta potential of the SSNPs was unaffected by the pH changes, indicating their stability during transit through the GI tract. Likewise, dilution of SSNPs with 0.15 M PBS (pH 6.8) up to 100-fold resulted in unappreciable change in their sizes or zeta potentials, indicating that SSNPs can withstand the extensive dilution by physiological fluids. Following treatment with mouse serum or intestinal fluids, SSNPs effectively preserved the siRNA integrity, substantiating their desired resistance against nuclease attack.

Figure 4:
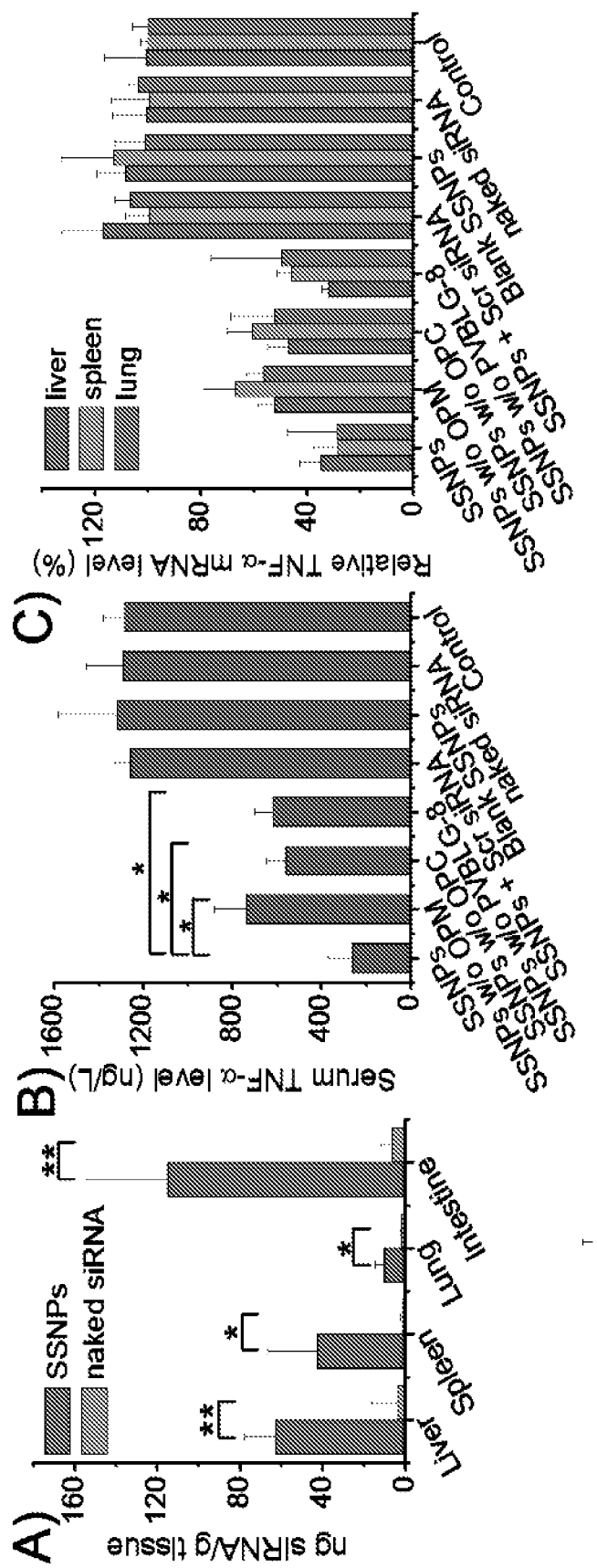
FIG. 4A-F. Orally delivered SSNPs mediate efficient RNAi against LPS-induced TNF-α production and protected mice from acute hepatic injury. (A) Biodistribution of DY800-siRNA 2 hours post oral gavage of SSNPs or naked DY800-siRNA (n =3). (B) Serum TNF-α level of mice gavaged with SSNPs at 200 μg siRNA/kg (n =6). (C) Relative TNF-α mRNA levels in mouse liver (left bar), spleen (middle bar), and lung (right bar) 24 hours after oral gavage of SSNPs (n =3). (D) Serum AST (left bar) and ALT (right bar) levels of mice 5 hours after LPS/D-GalN stimulation (n =4). (E) Survival of mice following oral gavage of SSNPs and i.p. injection of LPS/D-GalN 24 hours later (n =10); no LPS/D-GalN =top line; PBS +LPS/D-GalN=left line; SSNPs +LPS/D-GalN =right line. (F) HE-stained liver sections from mice 5 hours after LPS/D-GalN stimulation (bar =1 mm).
Figure 4:
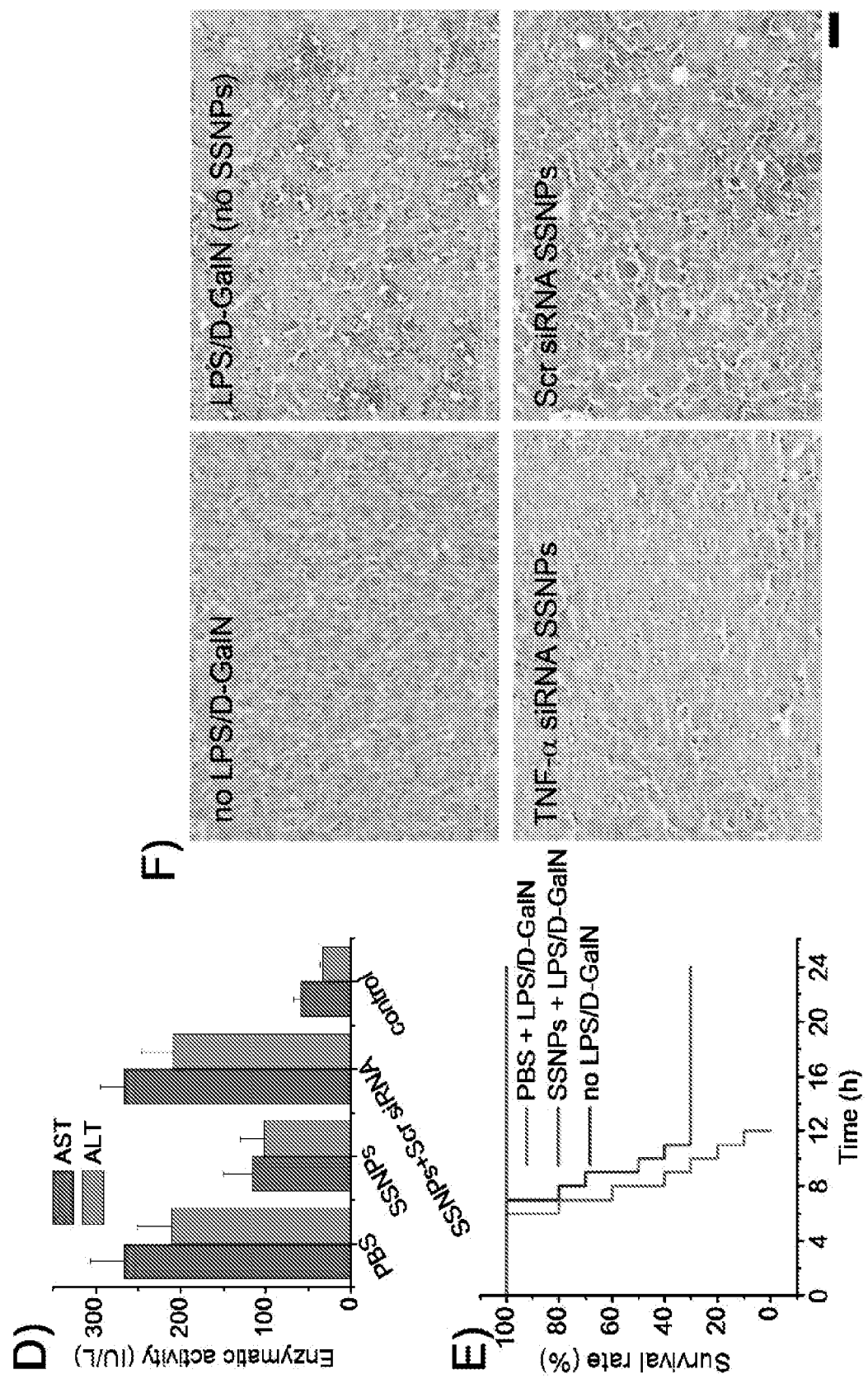

The biodistribution profiles of orally delivered SSNPs were then evaluated by using DY800-siRNA. SSNPs-treated mice experienced notably higher siRNA distribution levels in the liver, spleen, and lung than mice receiving naked siRNA (FIG. 4A). Combined with the observation of a ~20-fold higher siRNA level in the small intestine, it was demonstrated that SSNPs promoted both intestinal absorption and systemic translocation of siRNA. Single gavage of SSNPs at 200 µg TNF-α siRNA/kg reduced mouse serum TNF-α levels by 80% (FIG. 4B) and notably depleted TNF-α mRNA in macrophage-enriched organs (liver, spleen, and lung; FIG. 4C), indicating that the intestinally absorbed SSNPs had infiltrated and transfected macrophages in reticuloendothelial tissues to induce systemic TNF-α knockdown.

In accordance with the intestinal absorption levels and in vitro RNAi efficiencies, SSNPs without OPM, OPC, or PVBLG-8 showed significantly reduced in vivo silencing efficiency (FIGS. 4B and 4C), again substantiating the essential roles of individual components in mediating oral absorption and systemic gene knockdown. As a result of systemic TNF-α knockdown, orally delivered SSNPs displayed marked anti-inflammatory effects against LPS/D-GalN-induced acute hepatic injury.

LPS/D-GalN challenge elevated serum alanine transaminase (ALT) and aspartate aminotransferase (AST) levels (FIG. 4D), and caused animal lethality within 12 hours (FIG. 4E). Comparatively, SSNPs orally administered 24 hours before LPS/D-GalN stimulation significantly inhibited the elevation in serum ALT/AST levels and improved the survival rate. During necropsy, livers from control mice (only LPS/D-GalN treated) were found to have turned yellow or black, indicating severe lipid accumulation, liver steatosis, and hemorrhage. Conversely, in the SSNPs-treated mice, most of the livers remained normal reddish color, indicating alleviation of the hepatic injury.

Histological observation on HE-stained liver sections further confirmed the remarkable therapeutic efficacy of SSNPs in alleviating inflammatory symptoms, including congested central vein, infiltrated inflammatory cells, disarranged hepatocytes, and broken cytolemma (FIG. 4F). In FIG. 4F, the HE-stained liver section for TNF-α siRNA SSNPs was remarkably similar to the control (no LPS/D-GalN). It was also noted that 24 hours following oral administration of SSNPs, serumIL-1β, IL-6, TNF-α, and IFN-γ levels were not significantly increased, demonstrating that the SSNPs and TNF-α siRNA did not activate pro-inflammatory cytokines or induce IFN-γ responses.

Single gavage of SSNPs to induce marked TNF-α silencing at a low dose of 200 µg siRNA/kg demonstrated comparable efficacy to previously reported β1,3-$_D$-glucan particles (GeRPs), which required a cumulative dose of 160 µg siRNA/kg via oral administration within eight consecutive days. For clinical application, oral administration is clearly superior to i.p. or i.v. injections for existing siRNA delivery systems in treating TNF-α -associated hepatic injury. Although oral RNAi against TNF-α has been reported to treat bowel inflammation, the gene knockdown was localized intestinally rather than infiltrated systemically, presumably due to inefficient intestinal absorption. Therefore, SSNPs that mediate effective intestinal absorption and systemic TNF-α silencing rendered obvious advantages.

Figure 7:
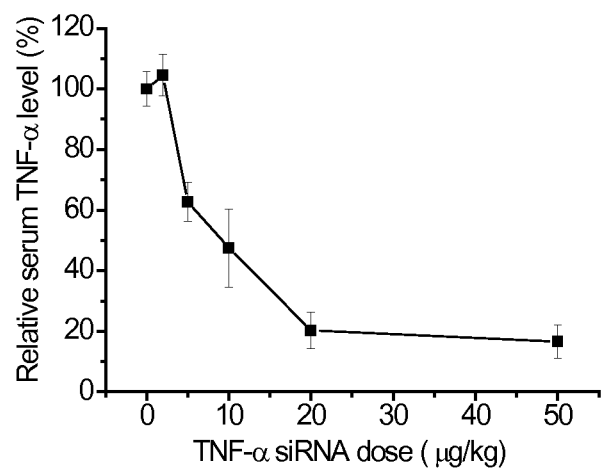
FIG. 7. TNF-α silencing efficiency of SSNPs following i.v. injection (n=3).

A relative pharmacological bioavailability of ~10% was noted compared to i.v. injection (comparable TNF-α silencing efficiency oral gavaged at 200 µg siRNA/kg and i.v. administered at 20 µg siRNA/kg, FIG. 7), indicating that oral administration represents an effective delivery route for systemic TNF-α silencing using multifunctional SSNPs. After SSNPs were intestinally absorbed by M cells, they could be directly transferred to the underlying GAMs, which infiltrated systemic reticuloendothelial tissues to exert systemic gene knockdown. With the OTMC/OPC-mediated mucoadhesion and OPM-mediated mannose-targeting, SSNPs can be efficiently taken up by M cells and thereafter can be directed to the underlying GAMs. Their excellent gene silencing capability thus allow for potent TNF-α knockdown in GAMs and macrophages enriched in the liver, spleen, and lung, ultimately leading to systemic TNF-α depletion.

Figure 8:
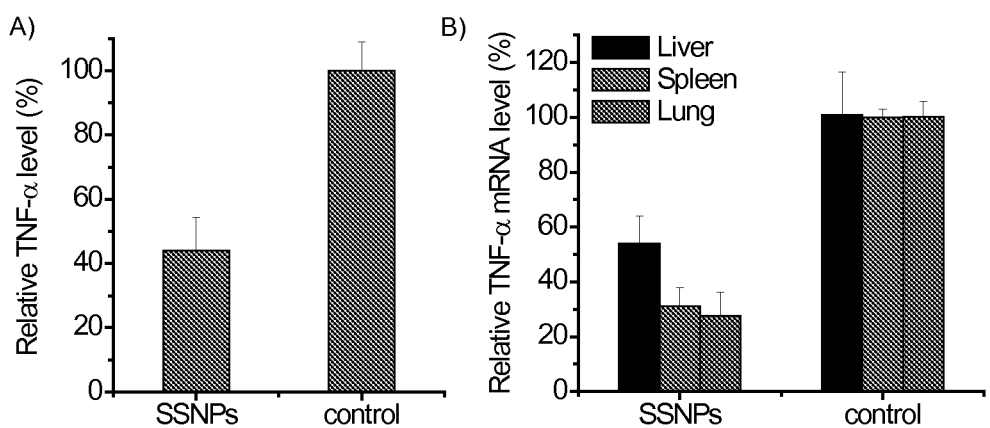
FIG. 8A-B. Serum TNF-α level (A) and TNF-α mRNA levels in the liver, spleen, and lung (B) following oral administration of SSNPs at 50 μg siRNA/kg (n =3).

Thus, multifunctional SSNPs are a new delivery system for siRNA cargo, where the particles display the specific functions of mucoadhesion, trans-epithelial permeation, membrane penetration, and active targeting, which collectively contributed to effective circumvention of the various gastrointestinal, systemic, and cellular barriers toward oral RNAi. No other nanoparticle-based delivery vehicle has thus far been reported to possess all of these attributes, making SSNPs the first example of a nanocarrier that simultaneously addresses the material requirements for mediating effective oral RNAi with an siRNA dose as low as 50 µg/kg (FIG. 8). The potent RNAi efficiency of SSNPs against systemic TNF-α production provides an exciting approach for the treatment of hepatic injury and other inflammatory diseases.

Oral Delivery of SSNPs Induced In Vivo RNAi Against Systemic Inflammation. TNF-α siRNA-containing SSNPs were orally gavaged to mice at 200 µg siRNA/kg (4 mice per group) with untreated mice serving as a control group. The gavage volume was 0.39 mL/mouse at the animal body weight of 20 g. Twenty-four hours post administration, LPS (12.5 µg/kg) and D-GalN (1.25 g/kg) were i.p. injected. Blood was collected 1.5 hours later to determine the serum TNF-α level by ELISA. For direct comparison with i.v. injection, SSNPs were also i.v. injected to mice at various siRNA doses.

In another experiment, mice were orally gavaged with SSNPs and i.p. challenged with LPS/D-GalN as described above. Five hours post LPS/D-GalN stimulation, blood was collected to evaluate the serum ALT as well as AST levels using commercial kits (Biovision Inc., San Francisco, Calif., USA). Mice were then sacrificed. Liver, spleen, and lung were harvested, cut into small pieces, washed with saline, and homogenized with Trizol reagent. RNA extraction was performed as described for RAW 264.7 cells. Intracellular TNF-α mRNA levels were monitored by real-time PCR. For histological evaluation, mouse liver was also harvested 5 hours post LPS/D-GalN stimulation, fixated in paraffin, cross-sectioned, and stained with haematoxylin/eosin (HE).

To evaluate the oral absorption and biodistribution profiles, SSNPs containing DY800-siRNA were orally gavaged to mice at 200 µg siRNA/kg (3 mice per group). Mice were sacrificed 2 hours post administration, and the liver, spleen, lung, and small intestine were harvested, washed with PBS, and fixed in 10% formalin before quantification of the fluorescent intensity in each organ using an Odyssey infrared mouse imaging system (800 nm emission). Organs from non-treated mice served as the blank. Biodistribution level in each organ was calculated from the calibration curve and represented as ng siRNA per gram tissue.

For lethality tests, mice (10 per group) were orally gavaged with SSNPs (200 µg siRNA/kg) or PBS. Twenty-four hours later, LPS/D-GalN was i.p. injected as described above. The survival of animals was monitored for 24 hours. Mice that received orally administered SSNPs without i.p. injection of LPS/D-GalN served as the control.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A nanoparticle comprising:
   a) siRNA;
   b) oley trimethly chitosan (OTMC);
   c) poly(γ-(4-(((2-(piperidin-1-yl)ethyl)amino)methyl) benzyl-L-glutamate) (PVBLG-8);
   d) oleyl-PEG-mannose(OPM);
   e) oleyl-PEG-cysteamine(OPC); and
   f) sodium tripolyphosphate(TPP);
   wherein the OTMC/TPP components of the nanoparticle are present in a ratio of about 8:1(w/w), the OTMC/OPM/OPC components of the nanoparticle are present in a ratio of about 1:1:1(w/w); and the nanoparticle has a diameter of about 100 nm to about 140 nm.

2. A pharmaceutical composition comprising a plurality of nanoparticles of claim 1 in combination with a pharmaceutically acceptable diluent, excipient, or carrier.

3. A method for orally delivering siRNA to a subject comprising orally administering the pharmaceutical composition of claim 1 to a subject, wherein the siRNA is delivered to cells of the lining of the digestive system of the subject.

4. The method of claim 3 wherein the siRNA is TNF-α siRNA.

5. The method of claim 4 wherein the endogenous production of tumor necrosis factor (TNF)-α in the subject is reduced by at least 50%.

6. The method of claim 5 wherein the administration treats or reduces the symptoms of an inflammatory disease.

7. The method of claim 6 wherein the inflammatory disease is lipopolysaccharide (LPS)-induced hepatic injury.

8. A method for TNF-α silencing in macrophages in a subject comprising administering to a subject an effective TNF-α silencing amount of a composition comprising a plurality of nanoparticles of claim 1, wherein the siRNA of the nanoparticles is delivered into macrophages of the subject and endogenous production of TNF-α in the subject is reduced by at least 50%.

9. A pharmaceutical composition for the oral delivery of siRNA comprising a plurality of siRNA-containing nanoparticles, wherein the nanoparticles comprise
   a) siRNA;
   b) oleyl trimethyl chitosan (OTMC);
   c) poly(γ-(4-(((2-(piperidin-1-yl)ethyl)amino)methyl) benzyl-L-glutamate) (PVBLG-8);
   d) oleyl-PEG-mannose(OPM);
   e) oleyl-PEG-cysteamine(OPC); and
   f) sodium tripolyphosphate(TPP);
   wherein the OTMC/PVBLG/siRNA componoents of the nanoparticle are present in a ratio of about 100:20:1 (w/w); the OTMC/TPP components of the nanoparticle are present in a ratio of about 8:1(w/w), the OTMC/OPM/OPC components of the nanoparticle are present in a ratio of about 1:1:1(w/w); and the nanoparticle has a diameter of about 100 nm to about 140 nm.

10. A pharmaceutical composition comprising a plurality of nanoparticles of claim 1 in combination with a pharmaceutically acceptable diluent, excipient, or carrier, wherein at least one diluent, excipient, or carrier is selected from water, ethanol, and a polyol.

11. A method for orally delivering siRNA to a subject comprising orally administering the pharmaceutical composition of claim 9 to a subject, wherein the siRNA is delivered to cells of the lining of the digestive system of the subject.

12. The method of claim 11 wherein the siRNA is TNF-α siRNA.

13. The method of claim 12 wherein the endogenous production of tumor necrosis factor (TNF)-α in the subject is reduced by at least 50%.

14. The method of claim 13 wherein the administration treats or reduces the symptoms of an inflammatory disease.

15. The method of claim 14 wherein the inflammatory disease is lipopolysaccharide (LPS)-induced hepatic injury.

16. A method for TNF-α silencing in macrophages in a subject comprising administering to a subject an effective TNF-α silencing amount of the composition of claim 9, wherein the siRNA of the nanoparticles is delivered into macrophages of the subject and endogenous production of TNF-α in the subject is reduced by at least 50%.

17. The pharmaceutical composition of claim 9 comprising water.

* * * * *

UNITED STATES PATENT AND TRADEMARK OFFICE
CERTIFICATE OF CORRECTION

PATENT NO. : 9,617,544 B2            Page 1 of 1
APPLICATION NO. : 14/783765
DATED : April 11, 2017
INVENTOR(S) : Cheng et al.

It is certified that error appears in the above-identified patent and that said Letters Patent is hereby corrected as shown below:

In the Claims

Claim 1, Column 37, Line 4, delete "oley" and insert -- oleyl -- therefor.

Claim 3, Column 37, Lines 20-21, delete "the pharmaceutical composition" and insert -- a plurality of nanoparticles -- therefor.

Claim 9, Column 38, Line 8, delete "componments" and insert -- components -- therefor.

Signed and Sealed this
Thirtieth Day of May, 2017

Michelle K. Lee
*Director of the United States Patent and Trademark Office*